United States Patent [19]

Takaki et al.

[11] Patent Number: 5,541,228

[45] Date of Patent: Jul. 30, 1996

[54] MELATONERGIC AGENTS

[75] Inventors: Katherine S. Takaki, Middletown; George N. Karageorge, Meriden; Daniel J. Keavy, Middletown; Michael F. Parker, Somers; Brett T. Watson, Wallingford, all of Conn.

[73] Assignee: Bristol-Myers Squibb Co., Princeton, N.J.

[21] Appl. No.: 376,328

[22] Filed: Mar. 8, 1995

Related U.S. Application Data

[63] Continuation of Ser. No. 323,293, Oct. 14, 1994, abandoned.

[51] Int. Cl.$^6$ .......................... A61K 31/16; C07C 233/05

[52] U.S. Cl. .......................... 514/630; 514/534; 514/538; 514/595; 514/624; 514/625; 514/627; 562/442; 564/47; 564/56; 564/184; 564/189; 564/190; 564/191; 564/192; 564/202; 564/204; 564/207

[58] Field of Search .................................. 564/184, 189, 564/190, 191, 202, 204, 207; 514/624, 625, 627, 629, 630

[56] References Cited

U.S. PATENT DOCUMENTS

| | | | |
|---|---|---|---|
| 4,859,706 | 8/1989 | Buerstinghaus et al. | 514/624 |
| 4,960,796 | 10/1990 | Neubauer et al. | 514/624 |
| 5,059,620 | 10/1991 | Stout et al. | 514/422 |
| 5,071,875 | 12/1991 | Horn et al. | 514/613 |
| 5,194,614 | 3/1993 | Andrieux et al. | 544/400 |
| 5,225,442 | 7/1993 | Andrieux et al. | 514/613 |
| 5,240,919 | 8/1993 | Yous et al. | 514/210 |
| 5,276,051 | 1/1994 | Lesieur et al. | 514/415 |
| 5,300,507 | 4/1994 | Yous et al. | 514/253 |
| 5,308,866 | 5/1994 | Lesieur et al. | 514/469 |
| 5,318,994 | 6/1994 | Andrieux et al. | 514/613 |
| 5,322,843 | 6/1994 | Yous et al. | 514/233.8 |
| 5,322,849 | 6/1994 | Yous et al. | 514/321 |
| 5,326,775 | 7/1994 | Yous et al. | 514/375 |

FOREIGN PATENT DOCUMENTS

| | | |
|---|---|---|
| 646968 | 2/1993 | Australia . |
| 35445/93 | 9/1993 | Australia . |
| 48729/93 | 4/1994 | Australia . |

| | | |
|---|---|---|
| WO94/07487 | 4/1994 | WIPO . |

OTHER PUBLICATIONS

Arendt et al, "Alleviation of Jet Lag by Melatonin: preliminary results of controlled double blind trial", Brit. Med. J., vol. 292, (1986) p. 1170.

Cassone et al, "Dose Dependent Entrainment of Rat Circadian Rythyms by Daily Injection of Melatonin", J. Biol. Rythyms, vol. 1, No. 3, (1986) pp. 219–229.

Copinga et al, "2–Amino–8–methoxytetralins: A series of Nonindolic Melatonin–like Agents", J. Med. Chem., 36, (1993) pp. 2891–2898.

Ebisawa et al, "Expression cloning of a high–affinity melatonin receptor from Xenopus dermal melanophores", Proc. Natl. Acad. Sci. USA, vol. 91, Jun. 1994) pp. 6133–6177.

Langlois, et al., "Design and Synthesis of New Naphthalenic Derivatives as Ligands for 2–[$^{125}$I]Iodomelatonin Binding Sites," J. Med. Chem., 38:2050–2060 (1995).

Primary Examiner—Shailendra Kumar
Attorney, Agent, or Firm—Sandra M. Nolan

[57] ABSTRACT

New melatonergic agents are phenyl alkanyl or phenyl alkyl substituted carboxamides and ureas of Formula I:

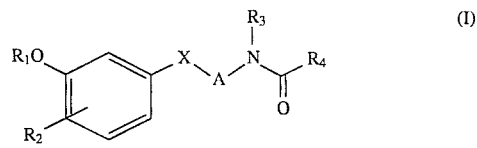

wherein:

$R_1 = C_{1-3}$ alkyl, allyl, $C_{3-6}$ cycloalkyl substituted $C_{1-4}$ alkyl;

$R_2$=hydrogen, halogen or $C_{1-4}$ alkoxy;

$R_3$=hydrogen or $C_{1-4}$ alkyl;

$R_4 = C_{1-4}$ alkyl, $C_{1-4}$ alkyl substituted amino, carboxylic acid substituted $C_{1-4}$ alkyl or $C_{3-6}$ cycloalkyl, $C_{3-6}$ cycloalkyl, or straight or branched chain $C_{2-4}$ alkenyl;

A=a linear $C_{2-4}$ alkanediyl or alkenediyl chain, provided that A not be —$CH_2CH_2$— when X is a bond; and X=a covalent bond or oxygen.

17 Claims, No Drawings

MELATONERGIC AGENTS

This is a continuation application of application Ser. No. 08/323,293, filed on Oct. 14, 1994, now abandoned.

BACKGROUND

The invention pertains to novel N-(phenylalkyl)amide and urea derivatives having drug and bio-affecting properties and to their preparation, pharmaceutical formulations and use. In particular, the invention concerns N-(phenylalkyl)amides and ureas having a metaalkoxy substituent in the phenyl ring. These compounds possess melatonergic properties that should make them useful in treating certain medical disorders.

Melatonin (N-acetyl-5-methoxytryptamine) is a hormone which is synthesized and secreted primarily by the pineal gland. Melatonin levels show a cyclical, circadian pattern with highest levels occurring during the dark period of a circadian light-dark cycle. Melatonin is involved in the transduction of photoperiodic information and appears to modulate a variety of neural and endocrine functions in vertebrates, including the regulation of reproduction, body weight and metabolism in photoperiodic mammals, the control of circadian rhythms and the modulation of retinal physiology.

Recent evidence demonstrates that melatonin exerts its biological effects through specific receptors. Use of the biologically active, radiolabelled agonist $[^{125}I]$-2-iodomelatonin has led to the identification of high affinity melatonin receptors in the CNS of a variety of species. The sequence of one such high affinity melatonin receptor, cloned from frog dermal melanophores, has been reported (Ebisawa, et al., *Proc. Natl. Acad. Sci.* 91:6133–6137, 1994). In mammalian brain, autoradiographic studies have localized the distribution of melatonin receptors to a few specific structures. Although there are significant differences in melatonin receptor distribution even between closely related species, in general the highest binding site density occurs in discreet nuclei of the hypothalamus. In humans, specific $[^{125}I]$-2-iodomelatonin binding within the hypothalamus is completely localized to the suprachiasmatic nucleus, strongly suggesting the melatonin receptors are located within the human biological clock.

Exogenous melatonin administration has been found to synchronize circadian rhythms in rats (Cassone, et al., *J. Biol. Rhythms,* 1:219–229, 1986). In humans, administration of melatonin has been used to treat jet-lag related sleep disturbances, considered to be caused by desynchronization of circadian rhythms (Arendt, et al., *Br. Med. J.* 292:1170, 1986). Further, the use of a single dose of melatonin to induce sleep in humans has been claimed by Wurtman in International Patent Application WO 94/07487. Thus, melatonin agonists should be particularly useful for the treatment of sleep disorders and other chronobiological disorders. Melatonin agonists would also be useful for the further study of melatonin receptor interactions as well as in the treatment of conditions affected by melatonin activity, such as depression, jet-lag, work-shift syndrome, sleep disorders, glaucoma, reproduction, cancer, immune disorders, and neuroendocrine disorders.

Aside from simple indole derivatives of melatonin itself, various bicyclic structures have been prepared and their use as melatonin ligands disclosed. In general these bicyclic amide structures can be represented as:

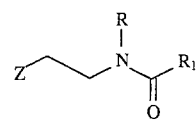

wherein Z is an aryl or heteroaryl system attached by a two carbon bridge to the amide group. Some specific examples follow.

Yous, et al. in European Patent Application EPA 527 687A disclose as melatonin ligands arylethylamines 1,

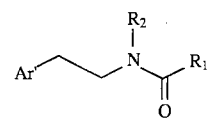

wherein Ar' is, inter alia, a substituted or unsubstituted benzo[b]thiophen- 3-yl, benzimidazol-1-yl, benzo[b]furan-3-yl, 1,2-benzisoxazol-3-yl, 1,2-benzisothiazol-3-yl, or indazol-3-yl radical; $R_1$ is, inter alia, an alkyl or cycloalkyl group; and $R_2$ is hydrogen or lower alkyl.

Horn and Dubocovich, in European Patent Application EPA 420 064A, disclose 2-amidotetralins 2 as melatonin ligands,

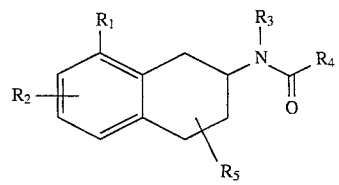

wherein $R_1$ is, inter alia, hydrogen, lower alkyl, or lower alkoxyl; $R_2$ is, inter alia, hydrogen, halogen, or lower alkoxyl; $R_3$ is, inter alia, hydrogen, or lower alkyl; $R_4$ is, inter alia, lower alkyl, haloalkyl or cycloalkyl; and $R_5$ is hydrogen, hydroxyl, halogen, oxo, aryl, lower alkyl or alkylaryl.

Yous, et al. in European Patent Application 506 539A claim melatonin ligands 3,

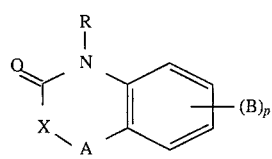

wherein A is oxygen or sulfur; X is a methylene group or a bond; and R is H or lower alkyl when p is 1 and B is defined by the radical 4,

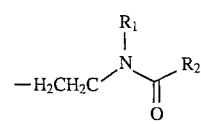

wherein $R_1$ is hydrogen or lower alkyl and $R_2$ is, inter alia, hydrogen, lower alkyl or cycloalkyl. Alternatively, R is defined by the radical 4 when p is 0 or 1 and B is lower alkoxy.

Several naphthalene derivatives have also been disclosed as melatonin ligands.

Andrieux, et al. in European Patent Application 447 285A claim amidoalkylnaphthalenes 5,

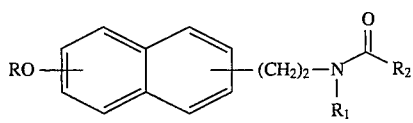

wherein R is lower alkyl; $R_1$ is hydrogen or lower alkyl; and $R_2$ is, inter alia, hydrogen, lower alkyl, or cycloalkyl.

Yous, et al. in European Patent Application 562 956A disclose amide and urea naphthalene derivatives 6,

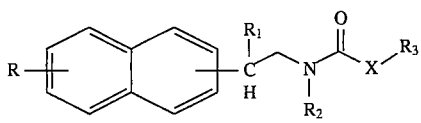

in which R is hydrogen or $OR_4$ wherein $R_4$ is, inter alia, hydrogen, alkyl, cycloalkyl, or cycloalkylalkyl; $R_1$ is hydrogen or $COOR_5$ wherein $R_5$ is hydrogen or alkyl; $R_2$ is hydrogen or alkyl; X is NH or a bond; and $R_3$ is, inter alia, alkyl, alkenyl, or cycloalkyl.

Lesieur, et al. in European Patent Application 530 087A disclose naphthylethylureas and naphthylethylthioureas 7,

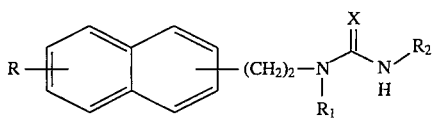

in which R is hydrogen or $OR_3$ wherein $R_3$ is, inter alia, hydrogen, lower alkyl, or cycloalkyl; $R_1$ is hydrogen or lower alkyl; X is oxygen or sulfur; and $R_2$ is, inter alia, lower alkyl or cycloalkyl.

Langlois, et al., in Australian Patent Application AU-A-48729/93 disclose arylalkyl(thio)amides 8 as melatonergic ligands,

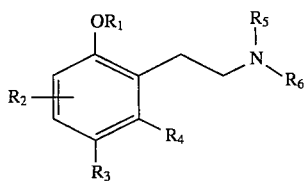

wherein $R_1$ is hydrogen or lower alkyl; $R_2$ is hydrogen, halogen, or lower alkyl; $R_3$ and $R_4$ are identical or different groups including, inter alia, hydrogen, halogen, or lower alkyl; $R_5$ is hydrogen or lower alkyl; and $R_6$ is,

wherein X is sulfur or oxygen and $R_7$ is, inter alia, lower alkyl or alkenyl. The disclosure specifies that the inventors have "discovered that new compounds of arylalkyl(thio)amide structures, substituted on their benzene ring with a hydroxyl or alkoxy radical specifically at the ortho position with respect to the alkyl(thio)amide chain, possessed very considerable activity with respect to the melatoninergic system, whereas these properties are not encountered with compounds substituted at the meta or para position with respect to the alkyl(thio)amide chain."

Copinga et al, in *J.Med, Chem.*, 1993, 36, p. 2891, discusses amidomethoxytetralins of structure 9 and their melatonergic properties.

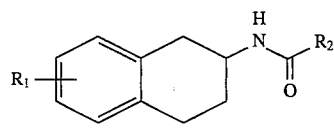

In structure 9, $R_1$ is H or $OCH_3$ and $R_2$ is alkyl, haloalkyl, phenylalkyl or phenyl.

In a comparative study, Copinga et al showed that compound 10 had markedly inferior $[^{125}I]$-2-iodomelatonin binding properties.

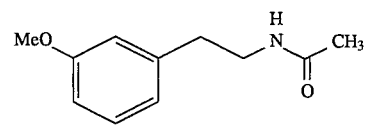

The foregoing disclosures do not teach or suggest the novel melatonergic phenylalkylamides or ureas of the present invention. The novel compounds of the present invention display enhanced melatonergic activity, in contradistinction to the prior art, with metasubstitution on the aryl ring and preferably a C3 or C4 bridge to the amide functionality.

SUMMARY OF THE INVENTION

Applicants have discovered a new group of melatonergic agents which conform to Formula I:

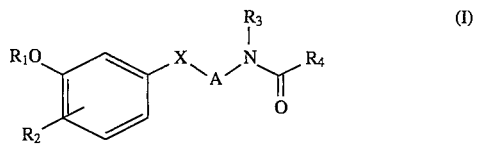

wherein:

$R_1=C_{1-3}$ alkyl, allyl, $C_{3-6}$ cycloalkyl substituted $C_{1-4}$ alkyl;

$R_2$=hydrogen, halogen or $C_{1-4}$ alkoxy;

$R_3$=hydrogen or $C_{1-4}$ alkyl;

$R_4=C_{1-4}$ alkyl, $C_{1-4}$ alkyl substituted amino, carboxylic acid substituted $C_{1-4}$ alkyl or $C_{3-6}$ cycloalkyl, $C_{1-4}$ alkoxy substituted $C_{1-4}$ alkyl, $C_{3-6}$ cycloalkyl, or straight or branched chain $C_{2-4}$ alkenyl;

A=a linear $C_{2-4}$ alkanediyl or alkenediyl chain, provided that A not be $-CH_2CH_2-$ when X is a bond; and X=a covalent bond or oxygen.

The melatonergic agents of the invention have several advantages over similar agents. They perform well in tests which demonstrate affinity for the melatonin binding site found in rabbit parietal cortex. Many of the compounds have $IC_{50}$ values for melatonin binding of 250 nM or less.

Further, the compounds are agonists as determined by their ability, like melatonin, to block the forskolin-stimulated accumulation of cAMP in certain cells.

In addition, several have been shown active in the "clock in the dish" test, an indicator of an agent's effectiveness in moderating the body's circadian rhythm.

These and other advantages will become apparent after consideration of the specification and claims.

DETAILED DESCRIPTION OF THE INVENTION

The melatonergic agents described herein conform to formula I:

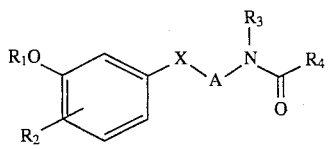

wherein:
- $R_1$=$C_{1-3}$ alkyl, allyl, $C_{3-6}$ cycloalkyl substituted $C_{1-4}$ alkanediyl;
- $R_2$=hydrogen, halogen or $C_{1-4}$ alkoxy;
- $R_3$=hydrogen or $C_{1-4}$ alkyl;
- $R_4$=$C_{1-4}$ alkyl, $C_{1-4}$ alkyl substituted amino, carboxylic acid substituted $C_{1-4}$ alkyl or $C_{3-6}$ cycloalkyl, $C_{1-4}$ alkoxy substituted $C_{1-4}$ alkyl, $C_{3-6}$ cycloalkyl, or straight or branched chain $C_{2-4}$ alkenyl;
- A=a linear $C_{2-4}$ alkanediyl or alkenediyl chain, provided that A not be —$CH_2CH_2$— when X is a bond; and
- X=a covalent bond or oxygen.

By "halogen," applicants mean Br, Cl, F and I.

The term "alkoxy", refers to alkyloxy groups with branched or straight chains.

By "amino", is meant $NR_5R_6$, wherein each of $R_5$ and $R_6$ may independently be hydrogen or $C_{1-4}$ alkyl.

The phrase "carboxylic acid substituted $C_{1-4}$ alkyl or $C_{3-6}$ cycloalkyl" refers to noncyclic $C_mH_{2m}$COOH or cyclic $C_{m'}H(2m'-2)$COOH groups, wherein m is 1 to 4 and m' is 3 to 6.

The term "$C_{1-4}$ alkoxy substituted $C_{1-4}$ alkyl" denotes monovalent alkyl-O-alkanediyl-groups in which both the alkyl and alkanediyl moieties contain from 1 to 4 carbon atoms.

By "alkanediyl" is meant saturated divalent groups containing only carbon and hydrogen.

By "alkenediyl" is meant cis- or trans- configured divalent ethylene groups containing one site of ethylenic unsaturation.

A cannot be an ethylene ($CH_2CH_2$) moiety when X is a direct bond.

In some preferred embodiments, compounds of formula II are used. Formula II is:

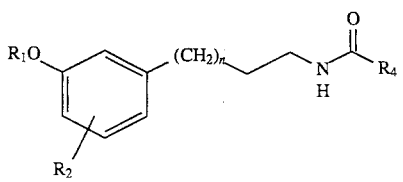

wherein $R_1$, $R_2$ and $R_4$ are as defined above and n=1 or 2. One preferred group of compounds are those in which $R_1O$ is a methoxy group. Compounds of Formula II in which $R_2$ is fluoro or chloro are also preferred.

These preferred compounds include:
- N-[3-(3-propoxyphenyl)propyl]butanamide;
- N-[3-(3-methoxyphenyl)propyl]cyclopropane carboxamide;
- N-[3-(3-methoxyphenyl)propyl]butanamide;
- N-[3-(3-methoxyphenyl)propyl]-N'-ethyl urea;
- N-[3-(3-methoxyphenyl)propyl]-2-methylpropanamide;
- N-[3-(3-methoxyphenyl)propyl]propenamide;
- N-[3-(3-methoxyphenyl)propyl]-2-methoxyacetamide;
- N-[3-(3-methoxyphenyl)propyl]propanamide;
- N-[3-(3-methoxyphenyl)propyl]acetamide;
- N-[3-(2-fluoro-5-methoxyphenyl)propyl]cyclopropane carboxamide;
- N-[3-(2-fluoro-5-methoxyphenyl)propyl]butanamide;
- N-[3-(2-fluoro-5-methoxyphenyl)propyl]-2-methylpropanamide;
- N-[3-(2-fluoro-5-methoxyphenyl)propyl]acetamide;
- N-[3-(4-chloro-3-methoxyphenyl)propyl]cyclopropane carboxamide;
- N-[3-(3-methoxyphenyl)propyl]-2-methylpropenamide;
- N-[4-(3-methoxyphenyl)butyl]-N'-methyl urea;
- N-[4-(3-methoxyphenyl)butyl]-N'-ethyl urea;
- N-[4-(3-methoxyphenyl)butyl]butanamide;
- N-[4-(3-methoxyphenyl)butyl]propanamide;
- N-[4-(3-methoxyphenyl)butyl]cyclopropane carboxamide;
- N-[4-(3-methoxyphenyl)butyl]acetamide;
- N-[4-(3-methoxyphenyl)butyl]-2-methylpropanamide;
- N-[3-(2,5-dimethoxyphenyl)propyl]butanamide;
- N-[3-(3-methoxyphenyl)propyl]-N'methyl urea;
- N-[3-(2,5-dimethoxyphenyl)propyl]cyclopropane carboxamide;
- N-[3-(3,4-dimethoxyphenyl)propyl]cyclopropane carboxamide;
- N-[3-(3,5-dimethoxyphenyl)propyl]butanamide;
- N-[3-(3,4-dimethoxyphenyl)propyl]butanamide;
- N-[3-(3-ethoxyphenyl)propyl]butanamide;
- N-[3-(3-cyclopropylmethoxyphenyl)propyl]butanamide;
- N-[3-(2,3-dimethoxyphenyl)propyl]butanamide;
- N-[4-(3-methoxyphenyl)butyl]cyclobutane carboxamide; and
- N-[3-(3-methoxyphenyl)propyl]pentamide.

In other preferred embodiments, compounds of formula III are used. Formula III is:

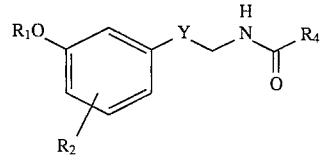

wherein $R_1$, $R_2$ and $R_4$ are as defined above and Y is an —$OCH_2$— radical or a cis- or trans- configured ethenediyl group. One preferred group of compounds are those in which $R_1O$ is a methoxy group. Compounds of Formula III in which $R_2$ is fluoro or chloro are also preferred.

These preferred compounds include:
- trans-N-[3-(2-fluoro-5-methoxyphenyl)-2-propenyl]-2-methylpropanamide;
- cis-N-[3-(2-fluoro-5-methoxyphenyl)-2-propenyl]-2-methylpropanamide;
- cis-N-[3-(2-fluoro-5-methoxyphenyl)-2-propenyl]butanamide;
- N-[2-(3-methoxyphenoxy)ethyl]butanamide; and
- N-[2-(3-methoxyphenoxy)ethyl]cyclopropane carboxamide.

Additionally, compounds of Formula I also encompass all pharmaceutically acceptable solvates, particularly hydrates, thereof. The present invention also encompasses geometric as well as optical isomers which arise as a consequence of structural asymmetry in certain compounds of Formula I. Separation of the individual isomers is accomplished by application of various methods which are well known to practitioners in the art.

The compounds of the invention are prepared using one or more of the following techniques:

SYNTHETIC ROUTES AND PROCEDURES

A. Synthesis of Final Acylated Derivatives

The preparation of all of the derivatives described herein involves an acylation of an appropriate amine. In most cases, this acylation is the final step in the synthetic sequence and is accomplished using one of the general procedures outlined below.

Scheme 1

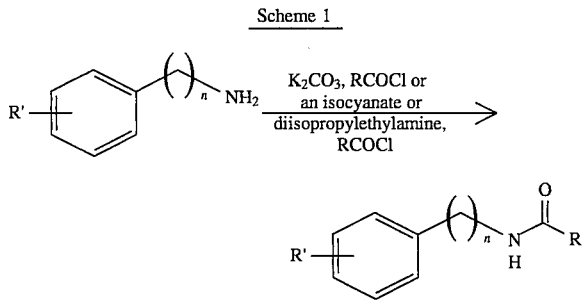

General Procedure A: A magnetically stirred suspension of the amine (4.54 mmol) and micropulverized potassium carbonate (5.00 mmol) in anhydrous acetonitrile (20 mL) at 5° C. was treated dropwise with a solution of the appropriate acyl chloride (5.00 mmol) in dry acetonitrile (5 mL). The suspension was stirred 0.5 h at 5° C., warmed to room temperature and stirred for 24 h. The suspension was poured over ice (50 g), treated with 5% sodium hydroxide solution (100 mL) and dichloromethane (100 mL). The layers were separated, the aqueous phase was back-extracted with fresh dichloromethane (3×75 mL), and the combined organic portions were washed with 5% hydrochloric acid solution (2×200 mL), 5% sodium hydroxide solution (2×200 mL), water (200 mL), saturated brine (200 mL), dried ($K_2CO_3$), filtered, and concentrated in vacuo. Alternatively, reactions have also been run using excess potassium carbonate (3–5 eq) and worked up by simple filtration through Celite and concentration in vacuo.

General Procedure B: A magnetically stirred solution of the amine (4.02 mmol) in 15 mL anhydrous methylene chloride at 5° C. was treated dropwise with a solution of the appropriate isocyanate (4.50 mmol) in dry dichloromethane (5 mL). The solution was stirred 0.5 h at 5° C, warmed to room temperature and stirred for 48 h. The suspension was poured over ice (50 g), treated with 5% sodium hydroxide solution (100 mL) and dichloromethane (100 mL). The layers were separated, the aqueous phase was back-extracted with fresh dichloromethane (3×75 mL), and the combined organic portions were washed with 5% hydrochloric acid solution (2×200 mL), 5% sodium hydroxide solution (2×200 mL), water (200 mL), saturated brine (200 mL), dried ($K_2CO_3$), filtered, and concentrated in vacuo. Alternatively, reactions have also been run in toluene at RT and worked up by simply concentrating in vacuo.

General Procedure C: The appropriate acid chloride (12 mmol) was added to a solution of the amine (12 mmol), and N,N-diisopropylethylamine (13.2 mmol) in 125 mL of $CH_2Cl_2$ at RT. The resulting mixture was stirred at RT overnight and then partitioned between water and $CH_2Cl_2$. The phases were separated and the aqueous phase was extracted with $CH_2Cl_2$ (3×100 mL). The combined organic layers were washed with brine (1×200 mL), dried over $MgSO_4$, filtered and concentrated in vacuo.

B. Synthesis of Amine Precursors

The amine precursors used in the above described acylation procedures were prepared as outlined below.

1. Synthesis of 3-Carbon Chain Amines

Most of the requisite amines containing a 3-carbon linking chain were prepared analogously to the route outlined below for the preparation of 3-methoxy-phenpropylamine but beginning with the appropriate benzaldehyde derivative. The starting benzaldehydes were commercially available with the exception of 3-methoxy-6-fluorobenzaldehyde which was prepared by the method described in: Furlano, D. C.; Calderon, S. N.; Chen, G.; Kirk, K. L. *J. Org. Chem.* 1988, 53, 3145–3147.

Scheme 2

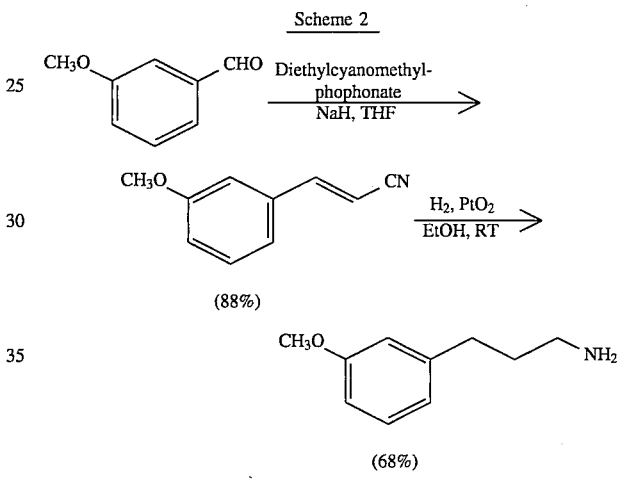

trans-3-(3-Methoxyphenyl)-2-propenenitrile: Diethylcyanomethyl phosphonate (28.6 mL, 176 mmol) was added to a suspension of NaH (7.0 g, 176 mmol, washed with hexanes to remove oil) in 450 mL of THF at RT and the resulting mixture was stirred at RT for 30 min. A solution of m-anisaldehyde (20.0 g, 140 mmol) in 50 mL of THF was added and the resulting mixture was stirred at RT overnight, resulting in the formation of a thick brown oil at the bottom of the mixture. The crude reaction mixture was concentrated in vacuo and the residue was partitioned between saturated aqueous. $NaHCO_3$ solution and methylene chloride. The organic phase was separated and the aqueous phase was extracted with methylene chloride. The combined organic phases were then dried over $MgSO_4$, filtered, and concentrated in vacuo to provide 27.6 g of a brown oil (99% crude yield) which was carried on without further purification. $^1$H NMR ($CDCl_3$) δ 7.30–7.40 (m, 2H), 6.92–7.05 (m, 3H), 5.86 (d, J=24 Hz, 1H), 3.85 (s,3H).

3-(3-Methoxyphenyl)propylamine: A mixture of trans-3-(3-Methoxyphenyl)-2-propenenitrile (27.6 g, 173 mmol) and $PtO_2$ (2.76 g) in 200 mL of EtOH and 30 mL of $CHCl_3$ was shaken in a Parr apparatus under an atmosphere of 50–60 psi $H_2$ overnight at RT. The reaction mixture was filtered through Celite and concentrated in vacuo to provide a brown solid which was then partitioned between $CH_2Cl_2$ and 1N NaOH. The organic phase was separated and the aqueous phase was extracted with $CH_2Cl_2$ (3×100 mL). The combined organic layers were then dried over MgSO₄, filtered and concentrated in vacuo to provide 24.2 g of the desired product as a yellow oil (85% yield). ¹H NMR (CDCl₃) δ 7.15–7.22 (m, 1H), 6.70–6.80 (m, 3H), 3.80 (s, 3H), 2.72 (t, J=6.0 Hz, 2H), 2.58–2.65 (m, 2H), 1.70–1.85 (m, 2H).

2. Synthesis of 4-(3-Methoxyphenyl)butylamine

The necessary amine precursor for all of the 4-carbon chain derivatives was prepared by the route outlined below.

Scheme 3

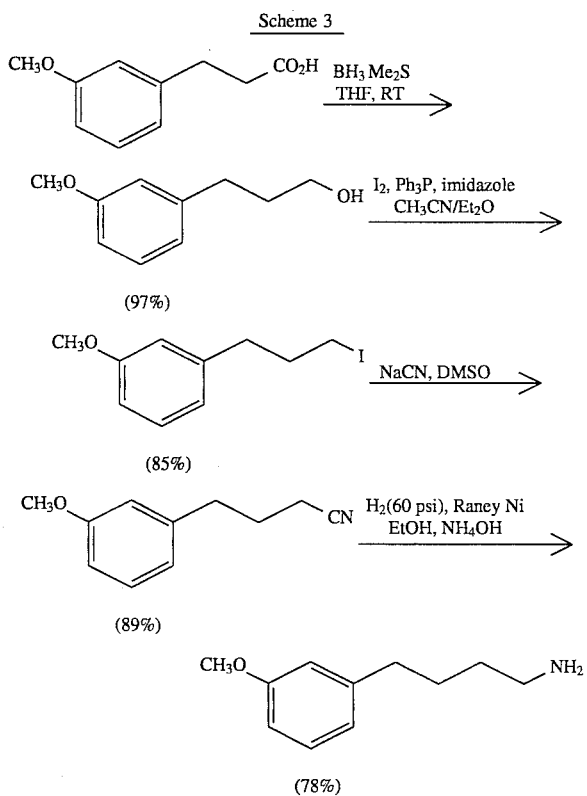

3-(3-Methoxyphenyl)propan-1-ol: A magnetically stirred solution of 3-(3-methoxyphenyl)propionic acid (71.38 g, 396.0 mmol) in 1.00 L of anhydrous tetrahydrofuran (THF) at room temperature was treated dropwise with a solution of borane-dimethyl sulfide (2.0M in THF, 680 mmol), stirred 1 h, heated at reflux for 2 h, cooled to room temperature, and stirred 12 h. The solution was poured over ice (300 g), treated with 6 N NaOH (500 mL), and stirred 1 h. The suspension was treated with diethyl ether (500 mL), the layers were separated, and the aqueous layer extracted with fresh diethyl ether (2×400 mL). The combined organic extracts were washed with water (500 mL), saturated sodium chloride solution (2×500 mL), dried (K₂CO₃), filtered, and concentrated in vacuo to give a clear liquid. Kugelrohr distillation (0.1 torr, 120° C.) gave 63.89 g (97%) of the alcohol: ¹H NMR (CDCl₃) δ 7.21 (t, J=8 Hz, 1H), 6.81–6.72 (m, 3H), 3.80 (s, 3H), 3.68 (t, J=7 Hz, 2H), 2.68 (t, J=8 Hz, 2H), 1.95–1.85 (m 2 H), 1.40 (bs, 1H).

3-(3-Methoxyphenyl)propyl iodide: A magnetically stirred solution of 3-(3-methoxyphenyl)propan-1-ol (62.48 g, 375.9 mmol), triphenylphosphine (128.6 g, 490.4 mmol), and imidazole (35.53 g, 516.7 mmol) in anhydrous acetonitrile (300 mL) / anhydrous diethyl ether (600 mL) at 5° C. was treated portion wise with iodine (136.20 g, 536.6 mmol). The yellow suspension turned orange with the last addition. The suspension was stirred 45 min, filtered, the cake washed with fresh diethyl ether (300 mL), the combined filtrate was concentrated in vacuo to 300 mL and diluted with diethyl ether (200 mL). The resultant organic solution was washed with saturated sodium thiosulfate (2×500 mL), saturated cupric sulfate (2×500 mL), brine (2×500 mL), filtered and concentrated in vacuo. The residue was digested with hexanes (300 mL), filtered and concentrated in vacuo. Kugelrohr distillation (0.1 torr, 120° C.) provided the desired product as a yellow liquid (88.10 g, 85%): ¹H NMR (CDCl₃) δ 7.20 (t, J=8 Hz, 1H), 6.81–6.73 (m, 3H), 3.81 (s, 3H), 3.17 (t, J=8 Hz, 2H), 2.70 (t, J=8 Hz, 2H), 2.14 (quint, J=8 Hz, 2 H).

4-(3-Methoxyphenyl)butyronitrile: A magnetically stirred suspension of sodium cyanide (13.65 g, 265 mmol) in anhydrous methyl sulfoxide (65 mL) was treated dropwise with 3-(3-methoxyphenyl)propyl iodide (66.25 g, 240 mmol) at a rate sufficient to keep the temperature below 45° C. The suspension was heated at 90° C. for 1 h, cooled to room temperature, poured over ice (1000 g), treated with diethyl ether (500 mL), the layers separated, and the aqueous portion back-extracted with diethyl ether (2×300 mL). The combined organic extracts were washed with water (3×500 mL), 6N HCl (500 mL), brine (500 mL), dried (MgSO₄), filtered, and concentrated in vacuo to a clear liquid. Kugelrohr distillation (0.1 torr, 120° C.) provided the desired product as a clear liquid (37.62 g, 89%): ¹H NMR (CDCl₃) δ 7.25 (t, J=8 Hz, 1H), 6.78–6.69 (m, 3H), 3.80 (s, 3H), 2.75 (t, J=8 Hz, 2H), 2.31 (t, J=8 Hz, 2H), 1.98 (quint, J=8 Hz, 2H).

4-(3-Methoxyphenyl)butylamine: To a Parr bottle flushed with nitrogen was added ~1.0 g of Raney Nickel (50% suspension in H₂O), ethanol (125 mL), ammonium hydroxide (30 mL), and a solution of 4-(3-methoxyphenyl)butyronitrile (8.49 g, 48.4 mmol) in ethanol (150 mL). The bottle was charged with hydrogen (60 psi) and rocked 3 d. The suspension was filtered through Celite, the cake rinsed with fresh ethanol (400 mL), and the combined filtrate concentrated in vacuo. The resulting suspension was treated with dichloromethane (200 mL) and water (200 mL), the layers separated, and the aqueous portion back-extracted with fresh dichloromethane (2×50 mL). The combined organic portions were washed with saturated sodium chloride solution (300 mL), dried (K₂CO₃), filtered, and concentrated in vacuo. Kugelrohr distillation (0.1 torr, 120° C.) provided the desired product as a clear liquid (6.77 g, 78%) which was identical spectroscopically to that previously reported. Venit, J. J.; DiPierro, M.; Magnus, P. J. *Org. Chem.* 1989, 54, 4298–4301. ¹H NMR (CDCl₃) δ 7.20 (t, J=8 Hz, 1H), 6.79–6.70 (m, 3H), 3.80 (s, 3H), 2.75–2.68 (m, 2H), 2.61 t J=8 Hz, 2H), 1.82–1.45 (m, 6H).

3. Synthesis of cis- and trans3-(2-Fluoro-5-methoxyphenyl)allylamine.

The allylic amines used for the preparation of the olefin derivatives were prepared by the route outlined below.

Scheme 4

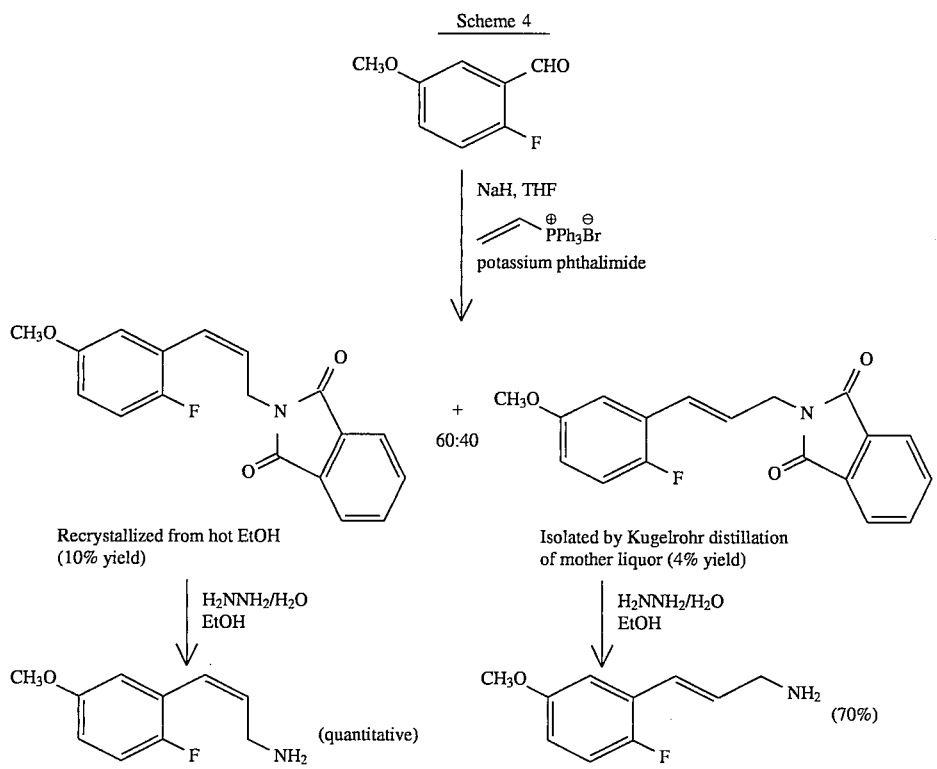

cis-2-[3-(2-Fluoro-5-methoxyphenyl)prop-2-en-1-yl]-isoindole-1,3-dione: A cold (0° C.) suspension of NaH (3.88 g, 97 mmol) and 2-fluoro-5-methoxy benzaldehyde (10.0 g, 65 mmol) in THF (400 mL) was treated with an admix of vinyltriphenylphosphonium bromide (31.2 g, 84.5 mmol) and potassium phthalimide (15.65 g, 84.5 mmol) under $N_2$. The reaction was then slowly heated to 45° C. for 1 h, followed by standing at ambient temperature for 18 h. The dark solution was quenched with 5% citric acid (25mL), then diluted with $H_2O$ (800 mL). The suspension was extracted with EtOAc (3×), the organics were combined and washed with 5% citric acid (3×), $H_2O$ (1×), brine, and dried over $K_2CO_3$. The crude oil was flashed through a plug of silica gel (toluene-2%MeOH/toluene) to afford pure material as a cis / trans mix (60/40, based on NMR). The cis compound was isolated by recrystallization from hot ethanol to give the titled cis isomer, 2.08 g, as a white solid, 10%: $^1$H NMR (300 MHz, $CDCl_3$) δ 3.82 (s, 3H), 4.48 (m, 2H), 5.76 (m, 1H), 6.56 (d, J=12.0 Hz, 1H), 6.70–7.05 (m, 3H), 7.68–7.86 (m, 4H); MS m/e 311; Analysis calc'd for $C_{18}H_{14}NO_3F$ 0.12(EtOH): C, 68.95; H, 4.78; N, 4.37; found: C, 69.23; H, 4.92; N, 4.37.

trans-2-[3-(2-Fluoro-5-methoxyphenyl )prop-2-en-1-yl ]-isoindole- 1,3-dione: Isolated from the synthesis of cis - 2-[3-(2-Fluoro-5-methoxyphenyl)prop-2-en-1-yl]-isoindole-1,3-dione by Kugelrohr distillation of the mother liquor, to afford the titled compound as a clear oil, 0.80 g, 4%.: m.p. 118°; $^1$H NMR (300 MHz, $CDCl_3$) δ 3.74 (s, 3H), 4.44 (dd, J=6.6, 1.2 Hz, 2H), 6.29 (m, 1H), 6.67–6.93 (m, 4H), 7.69–7.87 (m, 4H); MS m/e 311; Analysis calc'd for $C_{18}H_{14}NO_3F$: C, 69.45; H, 4.53; N, 4.50; found: C, 69.52; H, 4.59; N, 4.43.

cis-3-(2-Fluoro-5-methoxyphenyl)allylamine: Hydrazine hydrate (88%)(1.00 g, 19.2mmol) was slowly added to a stirring solution of cis - 2-[3-(2-fluoro-5-methoxyphenyl-)prop-2-en-1-yl]-isoindole-1,3-dione (2.00 g, 6.4 mmol) in EtOH (100 mL) and the solution was heated to reflux for 5 h. The resulting mixture was made acidic (pH<2.0) (10N HCl) followed by heating on a steam bath for 60 min. Cooling of the suspension to 0° C. precipitated the hydrazide which was filtered off, the filtrate was then diluted with $H_2O$ (20 mL) and extracted with EtOAc (2×). The aqueous layer was made basic (50% NaOH), and extracted with $Et_2O$ (3×). The ethereal layers were combined, washed with brine, dried over MgSO4, and concentrated to give a crude white wax. Purification by Kugelrohr distillation afforded the titled compound as a clear oil, 800mg, 70%: $^1$H NMR (300 MHz, $CDCL_3$) δ 1.26 (s, 2H, br), 3.421 (m, 2H), 3.78 (s, 3H), 5.81 (m, 1H), 6.40 (d, J=11.0 Hz, 1H), 6.62 (m, 2H), 6.90 (m, 1H).

trans-3-(2-Fluoro-5-methoxyphenyl)allylamine: Hydrazine hydrate (88%)(358 mg, 6.3 mmol) was slowly added to a stirring solution of trans - 2-[3-(2-fluoro-5-methoxyphenyl)prop-2-en-1-yl]-isoindole-1,3-dione (650 mg, 2.1 mmol) in EtOH (40mL) and the solution was heated to reflux for 5 h. The resulting mixture was made acidic (pH< 2.0) (10N HCl) followed by heating on a steam bath for 60 min. Cooling of the suspension to 0° C. precipitated the hydrazide which was filtered off, the filtrate was then diluted with $H_2O$ (20 mL) and extracted with EtOAc(2×). The aqueous layer was made basic (50% NaOH), and extracted with $Et_2O$(3×). The ethereal layers were combined, washed with brine, dried over $MgSO_4$, and concentrated to give a crude white wax. Purification by Kugelrohr distillation afforded the titled compound as a clear oil, 380 mg, quantitative: $^1$H NMR (300 MHz, $CDCl_3$) δ 1.49 (s, 2H, br), 3.43 (m, 2H), 3.71 (s, 3H), 5.75 (m, 1H), 6.28 (d, J=11.4 Hz, 1H), 6.65 (m, 2H), 6.90 (m, 1H).

4. Synthesis of 2-(3-methoxyphenoxy)ethyl amine:

Scheme 5

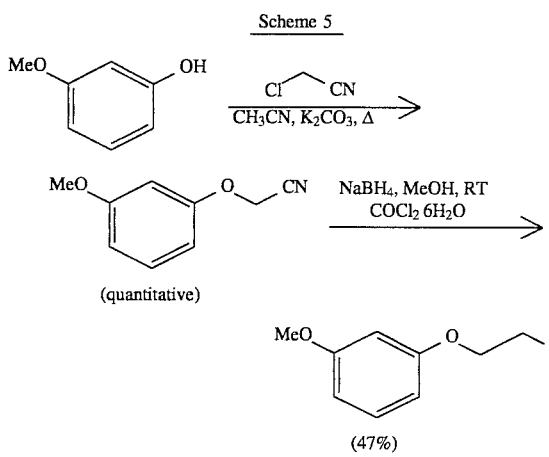

Chloroacetonitrile (5.1 ml, 81 mmol) was added to a suspension of 3-methoxyphenol (10 g, 81 mmol) and $K_2CO_3$ (22 g, 162 mmol) in 500 ml of acetonitrile. The resulting mixture was stirred at reflux temperature overnight, filtered through Celite, and concentrated at reduced pressure to give the desired nitrile as a brown oil in quantitative yield: $^1$H NMR (300 MHz, CDCl$_3$): 7.21–7.29 (m, 1H), 6.50–6.65 (m, 3H), 4.80 (s, 2H), 3.80 (s, 3H). Sodium borohydride (28 g, 74 mmol) was added to a solution of the nitrile (12 g, 740 mmol, 10 eq) and $CoCl_2 \cdot 6H_2O$ (35.2 g, 148 mmol, 2 eq) in 500 ml of methanol and stirred at RT overnight. The reaction mixture was quenched by the addition of HCl and concentrated under reduced pressure to give a yellow oil which was partitioned between ether and water. The aqueous layer was made alkaline with ammonium hydroxide and extracted with ether (3×200 ml). The ethereal extracts were washed with brine, dried over MgSO4, filtered, and concentrated under reduced pressure to give 5.8 g (47%) of the desired amine as a yellow oil which was used without further purification.

C. Other Synthetic Schemes

Other compounds of formula I were prepared as outlined in the schemes below.

Preparation of higher alkoxy derivatives:

Scheme 6

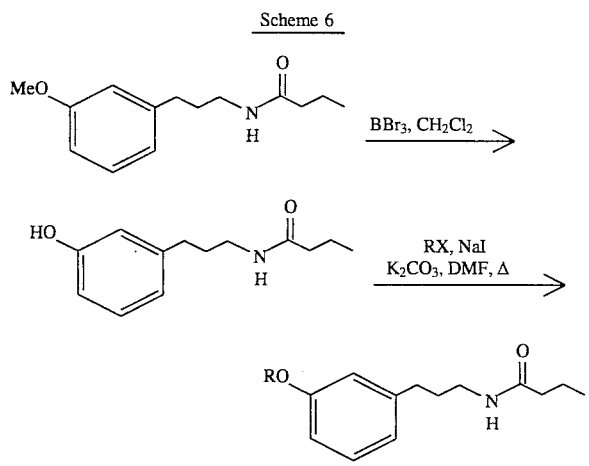

3-[3-(Hydroxyphenyl)propyl]butanamide: A solution of N-[3-(3-methoxyphenyl)propyl]butanamide (10 mmol) in 50 mL of $CH_2Cl_2$ was added to a mixture of $BBr_3$ (30 mmol) in 200 mL of $CH_2Cl_2$ at −78° C. The resulting reaction mixture was allowed to warm to RT with stirring overnight. The reaction mixture was quenched at 0° C. by the addition of water and neutralized with 3N NaOH. The crude mixture was then partitioned between water and $CH_2Cl_2$ and the organic phase separated. The aqueous phase was extracted with $CH_2Cl_2$ (3×200 mL) and the combined organic phases were dried over MgSO$_4$, filtered and concentrated in vacuo to provide a yellow oil in 81% yield. $^1$H NMR (300 MHz, CDCl$_3$) δ 7.09–7.14 (m, 1H), 6.65–6.71 (m, 3H), 5.42 (br s, 1H), 3.23–3.30 (m, 2H), 2.57 (t, J=7.4 Hz, 2H), 2.09 (t, J=7.2 Hz, 2H), 1.80 (quintet, J=7.2 Hz, 2H), 1.61 (sextet, J=7.4 Hz, 2H), 0.91 (t, J=7.3 Hz, 3H); IR (neat) 1640, 1550 cm$^{-1}$; MS (DCI, isobutane) m/e 443 (MH+M), 222 (MH).

General Procedure D: 3-[3-(Alkoxyphenyl)propyl]butanamides: The appropriate alkyl halide (1.7 eq) was added to a mixture of the phenol obtained above (1.0 eq), powdered potassium carbonate (3.9 eq), and a catalytic amount of NaI in DMF (final concentration =0.04–0.07M). The resulting mixture was heated at 50° C. for 1–4 h and then stirred at RT overnight. In some cases the reaction mixture was filtered through Celite and concentrated in vacuo to give the crude material. In other cases the reaction mixture was concentrated in vacuo and the residue partitioned between water and $CH_2Cl_2$. The aqueous phase was separated and extracted with $CH_2Cl_2$. The combined organic phases were then dried over MgSO$_4$, filtered and concentrated in vacuo to give the crude material.

Preparation of carboxylic acid derivatives:

Scheme 7

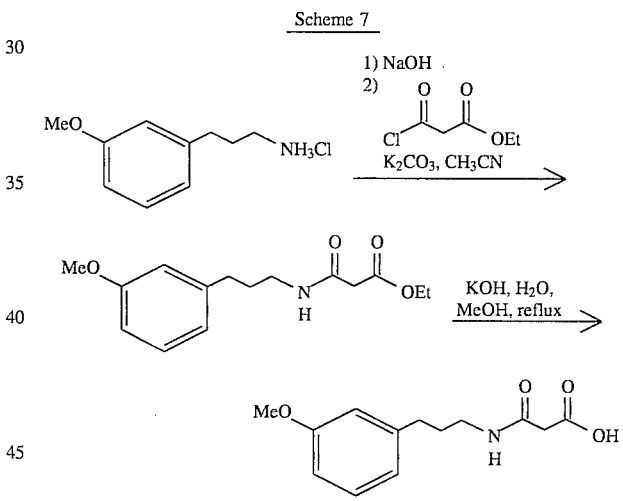

Administration

The compounds of the invention may be administered to patients in need of melatonergic treatment in a variety of ways. Thus, oral, transdermal, subcutaneous, intravenous, intramuscular, rectal, buccal, intranasal, and ocular routes can be used.

One or more of the compounds of the invention is mixed with pharmaceutically acceptable amounts of one or more conventional pharmaceutical excipients to produce a formulation to be administered by the desired route. Generally, such formulations will contain one or several carriers or diluents. Useful carriers include solids, semi-solids and liquids which have miscibility, or other compatability, with the active agent(s) so that they can deliver same to a patient or host.

Suitable carriers include lactose, dextrose, sucrose, sorbitol, mannitol, starches, gum acacia, calcium phosphate, alginates, tragacanth, gelatin, calcium silicate, micocrystalline cellulose, polyvinylpyrrolidone, cellulose, water, syrup, methyl cellulose, methyl- and propylhydroxybenzoates, talc, magnesium stearate, mineral oil and the like. Mixtures are operable.

Other useful excipients include lubricants, wetting agents, gellants, emulsifiers, preservatives, colorants, perfumes, flavor enhancers, drying agents and the like. Mixtures can be employed.

Generally, compositions which include the compounds of the invention will contain from about 0.10 to about 10% of active compound(s) and 99.9 to 90%, or other suitable amounts, of excipient(s).

Dosage levels will be dictated by the patient's needs and by the medical judgment of the treating physician. Generally, however, dosages of about 0.1 mg to about 100 mg per day are useful to treat sleep or circadian rhythm disorders.

While human patients are most preferred, the compounds of the invention may be used to treat other subjects, i.e., animals preferably mammals.

SPECIFIC EMBODIMENTS

The compounds which constitute this invention, their methods of preparation and their biologic actions will appear more fully from consideration of the following examples, which are given for the purpose of illustration only and are not to be construed as limiting the invention in sphere or scope. In the following examples, used to illustrate the foregoing synthetic processes, temperatures are expressed in degress Celsius and melting points are uncorrected. The nuclear magnetic resonances (NMR) are spectral characteristics refer to Chemical shifts ($\delta$) expressed as parts per million (ppm) versus tetramethylsilane (TMS) as reference standard. The relative area reported for the various shifts in the $^1$H NMR spectral data corresponds to the number of hydrogen atoms of a particular functional type in the molecule. The nature of the shifts as to multiplicity is reported as a broad singlet (bs), singlet (s), multiplet (m), doublet (d), or triplet (t). Abbreviations employed are DMSO-$d_6$ (deuterodimethylsulfoxide), CDCl$_3$ (deuterochloroform) and are otherwise conventional. The infrared (IR) spectral descriptions include only absorption wave numbers (cm$^{-1}$) having functional group identification value. The IR determinations were employed using the compound neat as a film or by employing potassium bromide (KBr) as diluent. The elemental analyses are reported as percent by weight. Unless otherwise noted, all percentages recited herein are weight percents, based on total composition weight.

The following examples describe in detail the preparation of compounds of Formula I. It will be apparent to those skilled in the art that modifications, both of materials and methods, will allow preparation of other compounds disclosed herein. From the foregoing description and the following examples it is believed that one skilled in the art is able to use the invention to the fullest extent.

EXAMPLES

Compounds of Formula I which were prepared by general procedure A.

Example 1

N-[3-(3-Methoxyphenyl)propyl]cyclopropane carboxamide.

Synthesized by General Procedure A. The crude material was purified by silica gel column chromatography using a 50% ethyl acetate/hexane eluant to provide an 18% yield of the desired product as a white solid. m.p. 65°–67° C.; $^1$H NMR (300 MHz, CDCl$_3$) $\delta$ 7.12–7.17 (m, 1H), 6.68–6.74 (m, 3H), 6.26 (bs, 1H), 3.73 (s, 3H), 3.24 (q, J=6, 12 Hz, 2H), 2.57 (t, J=9 Hz, 2H), 1.73–193 (m, 2H), 1.28–1.36 (m, 1H), 0.86–0.91 (m, 2H), 0.62–0.68 (m, 2H); $^{13}$C NMR (75 MHz, CDCl$_3$) $\delta$ 173.7, 159.6, 143.2, 129.3, 120.7, 114.1, 111.2, 55.1, 39.3, 33.3, 31.1, 14.5, 6.9; IR (KBr) 3300, 1640, 1550, 1260, 1040 cm$^{-1}$; MS (DCI) m/e 234(MH+), 467(MH+M); Analysis calc'd for C$_{14}$H$_{19}$NO$_2$*0.03 H$_2$O: C, 71.91; H, 8.22; N, 6.02; H$_2$O, 0.23; found: C, 71.56;H, 8.04;N, 6.02;H$_2$O, 0.6.

Example 2

N-[-3-(3-Methoxyphenyl)propyl]butanamide.

Synthesized by General Procedure A. The crude material was purified by silica gel column chromatography using a 40% ethyl acetate/hexane eluant to provide a 26% yield of the desired product as an oil. $^1$H NMR (300 MHz, CDCl$_3$) $\delta$ 7.20–7.15 (m, 1H), 6.76–6.70 (m, 3H), 5.39 (bs, 1H), 3.77 (s, 3H), 3.30–3.23 (m, 2H), 2.60 (t, J=7.4 Hz, 2H), 2.08 (t, J=7.2 Hz, 2H), 1.86–1.76 (m, 2 H), 1.62 (sextet, J=7.3 Hz, 2H), 0.91 (t, J=7.3 Hz, 3H); $^{13}$C NMR (75 MHz, CDCl$_3$)$\delta$ 172.9, 159.7, 143.1, 129.4, 120.7, 114.1, 111.2, 55.1, 39.1, 38.8, 33.4, 31.2, 19.2, 13.8; IR (KBr) 3294, 1644, 1552 cm$^{-1}$; MS (DCI) m/e 471 (MH+M), 236 (MH).

Example 3

N-[3-(2-Fluoro-5-methoxyphenyl)propyl]-2-methylpropanamide.

Synthesized by General Procedure A. The crude material was purified by Kugelrohr distillation (0.10 torr, T=150° C.) to provide a 47% yield of the desired product as a clear oil. $^1$H NMR (300 MHz, CDCl$_3$) $\delta$ 1.11 (d, J=6.9 Hz, 6H), 1.79 (quintet, J=7.5 Hz, 2H), 2.29 (t, J=6.9 Hz, 1H), 2.59 (t, J=7.2 Hz, 2H), 3.26 (quintet, J=6.9 Hz, 2H), 3.74 (s, 3H), 5.51 (s, 1H), 6.66 (m, 2H), 6.85 (t, J=9.4 Hz, 1H); IR (Film) 2968, 1646, 1546, 1500, 1468 cm$^{-1}$; MS m/e 253; Analysis calc'd for C$_{14}$H$_{20}$NO$_2$F: C, 66.38; H, 7.96; N, 5.53; found: C, 66.21; H, 8.00; N, 5.15.

Example 4

N-[3-(2-Fluoro5-methoxyphenyl)propyl]-acetamide.

Synthesized by General Procedure A: The crude material was purified by Kugelrohr distillation (0.10 torr, T=170° C.) to provide a 48% yield of the desired product as a clear oil. $^1$H NMR (300 MHz, CDCl$_3$) $\delta$ 1.76 (quintet, J=6.7 Hz, 2H), 1.93 (s, 3H), 2.61 (t, J=7.5 Hz, 2H), 3.23 (q, J=6.9 Hz, 2H),3.73 (s, 3H), 5.64 (s, 1H), 6.64 (m, 2H), 6.68 (t, J=5.8 Hz, 1H); IR (Film) 3300, 2968, 1646, 1500, 1210 cm$^{-1}$; MS m/e 225; Analysis calc'd for C$_{12}$H$_{16}$NO$_2$F 0.15 H$_2$O: C, 63.22; H, 7.21; N, 6.15; found: C, 63.17; H, 6.91; N, 6.39.

Example 5

N-[3-(2-Fluoro-5-methoxyphenyl)propyl]-butanamide.

Synthesized by General Procedure A: The crude material was purified by Kugelrohr distillation (0.10 torr, T=165° C.) to provide a 55% yield of the desired product as a clear oil. $^1$H NMR (300 MHz, CDCl$_3$) $\delta$ 0.91 (t, J=7.4 Hz, 3H), 1.60 (q, J=7.2 Hz, 2H), 1.74 (quintet, J=7.5 Hz, 2H), 2.10 (t, J=7.7 Hz, 2H), 2.60 (t, J=7.1 Hz, 2H), 3.26 (q, 6.8 Hz, 2H), 3.73 (s, 3H), 5.57 (s, 1H), 6.66 (m, 2H), 6.86 (t, J=6.8 Hz, 1H); IR (NaCl Film) 3300, 2968, 1646, 1500, 1210 cm$^{-1}$; MS m/e 253; Analysis calc'd for: C, 66.38; H, 7.96; N, 5.53; found: C, 66.05; H, 8.00; N, 5.40.

Example 6 cis-N-[3-(2-Fluoro-5-methoxyphenyl)-prop-2-enyl]-butanamide.

Synthesized by General Procedure A.: The crude material was purified by Kugelrohr distillation (0.10 torr, T=178° C.) to provide a 58% yield of the desired product as an oil. $^1$H NMR (300 MHz, CDCl$_3$) δ 0.94 (t, J=6.0 Hz, 3H), 1.66 (q, J=7.3 Hz, 2H), 2.12 (t, J=7.7 Hz, 2H), 3.78 (s, 3H), 4.03 (t, J=9.3 Hz, 2H), 5.55 (s, 1H), 5.76 (dt, J=6.9, 11.5 Hz, 1H), 6.48 (d, J=11.5 Hz, 1H), 6.68 (m, 2H), 6.88 (t, J=9.0 Hz, 1H); IR (NaCl Film) 3290, 2962, 1643, 1545, 1494, 1466, 1426, 1204 cm$^{-1}$; MS m/e 251; Analysis calc'd for C$_{14}$H$_{18}$NO$_2$F: C, 66.91; H, 7.22; N, 5.57; found: C, 66.57; H, 7.23; N, 5.59.

Example 7 cis-N-[3-(2-Fluoro-5-methoxyphenyl)-2-propenyl]-2-methylpropanamide.

Synthesized by General Procedure A. The crude material was purified by Kugelrohr distillation (0.10 torr, T=170° C.) to provide a 47% yield of the desired product as a clear oil. $^1$H NMR (300 MHz, CDCl$_3$) δ 1.13 (d, J=6.0 Hz, 6H), 2.33 (quintet, J=6.9 Hz, 1H), 3.78 (s, 3H), 4.00 (t, J=9.2 Hz, 1H), 5.55 (s, 1H), 5.77 (dt, J=6.9, 11.4 Hz, 1H), 6.48 (d, J=11.4 Hz, 1H), 6.68 (m, 2H), 6.88 (t, J=9.2 Hz, 1H); IR (Film) 3293, 2969, 1468, 1235, 1204 cm$^{-1}$; MS m/e 251; Analysis calc'd for C$_{14}$H$_{18}$NO$_2$F 0.15(H$_2$O): C, 66.20; H, 7.26; N, 5.52; found: C, 66.01; H, 7.27; N, 5.59.

Example 8

N-[3-(2,5-Dimethoxyphenyl)propyl]butanamide.

Synthesized by General Procedure A. The crude material was purified by silica gel column chromatography using a 50% ethyl acetate/hexane eluant to provide a 60% yield of the desired product as a white semi-solid. $^1$H NMR (300 MHz, CDCl$_3$) δ 6.63–6.75 (m, 3H), 5.84 (bs, 1H), 3.73 (s, 3H), 3.70 (s, 3H), 3.19 (dd, J=6, 9 Hz, 2H), 2.58 (t, J=6 Hz, 2H), 2.08 (t, J=9 Hz, 2H), 168–1.78 (m, 2H), 1.54–1.66 (m, 2H), 0.89 (t, J=7 Hz, 3H); $^{13}$C NMR (75 MHz, CDCl$_3$) δ 172.8, 153.5, 151.5, 131.0, 116.2, 111.3, 111.1, 55.9, 55.6, 38.8, 38.7, 29.8, 27.3, 19.2, 13.7; IR (KBr) 3300, 1650, 1555, 1230, 1050 cm$^{-1}$; MS (DCI) m/e 266 (MH+), 531 (MH+M).

Example 9

N-[3-(3-methoxyphenyl)propyl]-2-methyl-propanamide.

Synthesized by General Procedure A. The crude material was purified by silica gel column chromatography using a 50% ethyl acetate/hexane eluant to provide a 20% yield of the desired product as a yellow oil. $^1$H NMR (300 MHz, CDCl$_3$) δ 7.09–7.17 (m, 1H), 6.65–6.70 (m, 3H), 6.16 (bs, 1H), 3.70 (s, 3H), 3.15 (q, J=6, 6 Hz, 2H), 2.54 (t, J=7 Hz, 2H), 2.21–2.34 (m, 1H), 1.70–1.80 (m, 2H), 1.05 (d, J=7 Hz, 6H); $^{13}$C NMR (75 MHz, CDCl$_3$) δ 177.1, 159.6, 143.2, 129.3, 120.7, 114.1, 111.1, 55.0, 39.0, 35.4, 33.2, 31.1, 19.2; IR (KBr) 3300, 1640, 1550, 1260, 1040, 775 cm$^{-1}$; MS (DCI) m/e 236 (MH+), 471 (MH+M); Analysis calc'd for C$_{14}$H$_{21}$NO$_2$: C, 71.46; H, 8.99; N, 5.95; found: C, 71.26; H, 8.91; N, 5.86.

Example 10

N-[3-(3-Methoxyphenyl)propyl]-2-methyl-propenamide.

Synthesized by General Procedure A. The crude material was purified by silica gel column chromatography using a 90% ethyl acetate/hexane eluant to provide an 11% yield of the desired product as a colorless oil. $^1$H NMR (300 MHz, CDCl$_3$) δ 7.10–7.15 (m, 1H), 6.65–6.72 (m, 3H), 6.24 (bs, 1 H), 5.57 (t, J=0.9 Hz, 1H), 5.20–5.23 (m, 1H), 3.71 (s, 3H), 3.20–3.30 (m, 2H), 2.57 (t, J=9 Hz, 2H), 1.76–1.89 (m, 5H); $^{13}$C NMR (75 MHz, CDCl$_3$) δ 168.5, 159.7, 143.2, 140.1, 129.4, 120.7, 119.2, 114.1, 111.3, 55.1, 39.4, 33.5, 30.9, 18.6; IR (KBr) 3300, 1650, 1610, 1530, 1260, 1040 cm$^{-1}$; MS (DCI) m/e 234(MH+), 467(MH+M); Analysis calc'd for C$_{14}$H$_{19}$NO$_2$/0.05 H$_2$O; C, 71.77; H, 8.22; N, 5.98; H$_2$O, 0.42; found: C, 71.37; H, 8.24; N, 5.63; H$_2$O, 0.05.

Example 11

N-[4-(3-Methoxyphenyl)butyl]butanamide.

Synthesized by General Procedure A. Kugelrohr distillation (0.1 torr) gave the product as a clear oil in 64% yield: IR (film) 3296, 2936, 1644, 1602, 1584, 1550, 1262, 1044, 780 cm$^{-1}$; $^1$H NMR (300 MHz, CDCl$_3$) δ 7.16 (add, J=7.9, 7.9, 1.3 Hz, 1H), 6.75–6.69 (m, 2H), 6.69 (s, 1H), 5.55 (bs, 1H), 3.76 (s, 3H), 3.23 (td, J=7.0, 6.8 Hz, 2 H), 2.58 (t, J=7.4 Hz, 2H), 2.09 (t, J=7.4 Hz, 2H), 1.65–1.44 (m, 6H), 0.90 (t, J=7.4 Hz, 3H); MS m/z 250 (M$^+$+1); Anal. Calc'd for C$_{15}$H$_{23}$NO$_2$.0.13 H$_2$O: C, 71.58; H, 9.32; N, 5.57. Found: C, 71.60; H, 9.09; N, 5.49.

Example 12

N-[4-(3-Methoxyphenyl)butyl]propanamide.

Synthesized by General Procedure A. Kugelrohr distillation (0.1 torr) gave the product as a clear oil in 75% yield: IR (film) 3296, 2938, 1644, 1602, 1584, 1550, 1262, 1044, 780 cm$^{-1}$; $^1$H NMR (300 MHz, CDCl$_3$) δ 7.16 (ddd, J=7.9, 7.9, 1.3 Hz, 1H), 6.75–6.69 (m, 2H), 6.69 (s, 1H), 5.54 (bs, 1H), 3.76 (s, 3H), 3.23 (td, J=7.0, 6.8 Hz, 2H), 2.58 (t, J=7.4 Hz, 2H), 2.16 (q, J=7.4 Hz, 2H), 1.67–1.44 (m, 4H), 1.11 (t, J=7.6 Hz, 3H); MS m/z 236 (M$^+$+1); Anal. Calc'd for C$_{14}$H$_{21}$NO$_2$: C, 71.45; H, 9.00; N, 5.95. Found: C, 71.16; H, 8.80; N, 5.85.

Example 13

N-[4-(3-Methoxyphenyl)butyl]cyclopropane carboxamide.

Synthesized by General Procedure A. Kugelrohr distillation (0.1 torr) gave the product as a clear oil in 71% yield: IR (film) 3296, 2938, 1642, 1602, 1584, 1554, 1260, 1044, 770 cm$^{-1}$; $^1$H NMR (300 MHz, CDCl$_3$) δ 7.17 (ddd, J=7.9, 7.9, 1.3 Hz, 1H), 6.75–6.69 (m, 2H), 6.69 (s, 1H), 5.67 (bs, 1H), 3.77 (s, 3H) 3.25 (td, J=7.0, 6.8 Hz, 2H), 2.59 (t, J=7.4 Hz, 2H), 1.68–1.46 (m, 4 H), 1.31–1.23 (m, 1H), 0.95–0.90 (m, 2H), 0.71–0.65 (m, 2H); MS m/z 248 (M$^+$+1); Anal Calcd for C$_{15}$H$_{21}$NO$_2$.0.08 H$_2$O: C, 72.42; H, 8.57; N, 5.63. Found: C, 72.39; H, 8.43; N, 5.48.

Example 14

N-[4-(3Methoxyphenyl)butyl]acetamide.

Synthesized by General Procedure A. Kugelrohr distillation (0.1 torr) gave the product as a clear oil in 78% yield: IR (film) 3292, 2936, 1652, 1602, 1584, 1556, 1266, 1044 cm$^{-1}$; $^1$H NMR (300 MHz, CDCl$_3$) δ 7.16 (ddd, J=7.9, 7.9, 1.3 Hz, 1H), 6.74–6.69 (m, 2H), 6.69 (s, 1H), 5.61 (bs, 1H), 3.76 (s, 3H), 3.22 (td, J=7.0, 6.8 Hz, 2H), 2.57 (t, J=7.4 Hz, 2H), 1.92 (s, 3H), 1.64–1.44 (m, 4H); MS m/z 222 (M$^+$+1); Anal. Calcd for $C_{13}H_{19}NO_2$: C, 70.55; H, 8.65; N, 6.33. Found: C, 70.28; H, 8.62; N, 6.10.

Example 15

N-[3-(3-Methoxyphenyl)propyl]-2-methoxyacetamide.

Synthesized by General Procedure A. The crude material was purified by silica gel column chromatography using ethyl acetate as the eluant to provide a 17% yield of the desired product as a clear oil. $^1$H NMR (300 MHz, CDCl$_3$) δ 7.11–7.17 (m, 1H), 6.67–6.73 (m, 3H), 6.54 (bs, 1H), 3.81 (s, 2H), 3.73 (s, 3H), 3.33 (s, 3H), 3.24–3.30 (m, 2H), 2.58 (t, J=9 Hz, 2H), 1.75–1.85 (m, 2H); $^{13}$C NMR (75 MHz, CDCl$_3$) δ 169.4, 159.7, 142.9, 129.4, 120.7, 114.1, 111.3, 71.9, 59.1, 55.1, 38.4, 31.0; IR (KBr) 3350, 1675, 1535, 1260, 1120 cm$^{-1}$; MS (DCI) m/e 238 (MH+); Analysis calc'd for $C_{13}H_{19}NO_3$: C, 65.80; H, 8.07; N, 5.90; found: C, 65.84; H, 7.84; N, 5.84.

Example 16

N-[4-(3-Methoxyphenyl)butyl]pentanamidel.

Synthesized by General Procedure A. Kugelrohr distillation (0.1 torr) gave the product as a clear oil in 71% yield: IR (film) 3294, 2934, 1644, 1602, 1584, 1552, 1264, 1044 cm$^{-1}$; $^1$H NMR (300 MHz, CDCl$_3$) δ 7.17 (ddd, J=7.9, 7.9, 1.3 Hz, 1H), 6.75–6.69 (m, 2H), 6.69 (s, 1H), 5.52 (bs, 1H), 3.77 (s, 3H), 3.23 (td, J=7.0, 6.8 Hz, 2H), 2.58 (t, J=7.4 Hz, 2H), 2.12 (t, J=7.6 Hz, 2H), 1.67–1.44 (m, 6H), 1.30 (sext, J=7.4 Hz, 2H), 0.88 (t, J=7.3 Hz, 3H); MS m/z 264 (M$^+$+1); Anal. Calcd for $C_{16}H_{25}NO_2$: C, 72.97; H, 9.57; N, 5.32. Found: C, 72.58; H, 9.70; N, 5.55.

Example 17

N-[4-(3-Methoxyphenyl)butyl]-2-methyl-propanamide.

Synthesized by General Procedure A. Kugelrohr distillation (0.1 torr) gave the product as a clear oil in 77% yield: IR (film) 3298, 2934, 1644, 1602, 1584, 1548, 1260, 1044 cm$^{-1}$; $^1$H NMR (300 MHz, CDCl$_3$) δ 7.17 (ddd, J=7.9, 7.9, 1.3 Hz, 1H), 6.75–6.70 (m, 2H), 6.69 (s, 1H), 5.52 (bs, 1 H), 3.77 (s, 3 H), 3.23 (td, J = 7.0, 6.8 Hz, 2H), 2.59 (t, J=7.4 Hz, 2H), 2.28 (sept, J=6.9 Hz, 1H), 167–1.45 (m, 4H), 1.11 (d, J=6.9 Hz, 6H); MS m/z 250 (M$^+$+1); Anal. Calcd for $C_{15}H_{23}NO_2 \cdot 0.11 H_2O$: C, 71.68; H, 9.31; N, 5.57. Found: C, 71.67; H, 9.07; N, 5.55.

Example 18

N-[3-(2,3-Dimethoxyphenyl)propyl]butanamide

Synthesized by General Procedure A. The crude material was purified by silica gel column chromatography using a 50% ethyl acetate/hexane eluant to provide a 24% yield of the desired product as a pale yellow oil. $^1$H NMR (300 MHz, CDCl$_3$) δ 6.91 (t, J=6 Hz, 1H), 6.67–6.71 (m, 2H), 6.16 (bs, 1H), 3.77 (s, 3H), 3.75 (s, 3H), 3.10–3.21 (m, 2H), 2.59 (t, J=9 Hz, 2H), 2.06 (t, J =9 Hz, 2H), 1.66–1.76 (m, 2H), 1.51–1.63 (m, 2H), 0.86 (t, J=6 Hz, 3H); $^{13}$C NMR (75 MHz, CDCl$_3$) δ 172.9, 152.6, 146.9, 135.1, 124.1, 121.9, 110.3, 60.6, 55.6, 38.7, 38.5, 30.4, 26.8, 19.2, 13.7; IR (KBr) 3600–2500, 1650, 1550, 1260, 1010 cm$^{-1}$; MS (DCI) m/e 266 (MH+), 531 (MH+M); Analysis calc'd for $C_{15}H_{23}NO_3$: C, 67.90; H, 8.74; N, 5.28; found: C, 67.91; H, 8.75; N, 5.25.

Example 19

N-[2-(3-Methoxyphenoxy)ethyl]butanamide.

Synthesized by General Procedure A. The crude material was purified by silica gel column chromatography using 50% ethyl acetate/hexane eluant to provide a 31% yield of the desired product as a yellow oil. $^1$H NMR (300 MHz, CDCl$_3$) δ 7.15 (t, J=8.1 Hz, 1H), 6.41–6.51 (m, 3H), 5.99 (br s, 1H), 3.98 (t, J=5.0 Hz, 2H), 3.75 (s, 3H), 3.59–3.64 (m, 2H), 2.14 (t, J=7.3 Hz, 2H), 1.63 (sextet, J=7.4 Hz, 2H), 0.93 (t, J=7.3 Hz, 3H); $^{13}$C NMR (75 MHz, CDCl$_3$) δ 173.1, 160.8, 159.7, 130.0, 106.6, 106.5, 101.0, 66.9, 55.2, 38.8, 38.6, 19.1, 13.7; IR (neat) 3296, 1646, 1548 cm$^{-1}$; MS (DCI, isobutane) m/e 475 (2M+H), 351, 238 (MH), 114; Analysis calc'd for $C_{13}H_{19}NO_3$: C, 65.80; H, 8.07; N, 5.90; found: C, 65.64; H, 8.40; N, 5.89.

Example 20

N-[4-(3-Methoxyphenyl)butyl]cyclopentane carboxamide

Synthesized by Method A. Kugelrohr distillation (0.1 torr) gave the product as a waxy solid in 71% yield: LR (KBr) 3298, 2940, 1642, 1602, 1584, 1548, 1262, 1044, 778 cm$^{-1}$; $^1$H NMR (300 MHz, CDCl$_3$) δ 7.17 (ddd, J=7.9, 7.9, 1.3 Hz, 1H), 6.75–6.69 (m, 2H), 6.69 (s, 1H), 5.44 (bs, 1H), 3.77 (s, 3H), 3.23 (td, J=7.0, 6.8 Hz, 2H), 2.59 (t, J=7.4 Hz, 2H), 2.47–2.39 (m, 1H), 1.85–1.49 (m, 12 H); MS m/z 276 (M$^+$+1); Anal. Calcd for $C_{17}H_{25}NO_2$: C, 74.14; H, 9.15; N, 5.09. Found: C, 74.11; H, 8.95; N, 5.06.

The following compounds of Formula I were also prepared using the General Procedure A.

TABLE 1

| Ex. | Name | mp (°C.) |
| --- | --- | --- |
| 21 | N-[3-(2-Fluoro-5-methoxyphenyl)propyl]-cyclopropane carboxamide | 67–69 |
| 22 | trans-N-[3-(2-Fluoro-5-methoxyphenyl)-2-propenyl]-2-methylpropanamide | 80–81 |
| 23 | N-[3-(2,5-dimethoxyphenyl)propyl]-cyclopropane carboxamide | 86–88 |
| 24 | N-[3-(3-Methoxyphenyl)propyl]propenamide | 43–45 |
| 25 | N-[3-(3,4-Dimethoxyphenyl)propyl]-cyclopropane carboxamide | 54–55 |
| 26 | N-[3-(3,5-Dimethoxyphenyl)propyl]-butanamide | 35–36 |
| 27 | N-[3-(3,4-Dimethoxyphenyl)propyl]-butanamide | 38–39 |
| 28 | N-[4-(3-Methoxyphenyl)butyl]cyclobutane carboxamide | 45–46 |
| 29 | N-[3-(3-Methoxyphenyl)propyl]pentanamide | 30–31 |
| 30 | N-[3-(4-Chloro-3-methoxyphenyl)propyl]-cyclopropane carboxamide | 76–77 |
| 31 | N-[2-(3-Methoxyphenoxy)ethyl]cyclopropane carboxamide | 61–62 |

Compounds of Formula I which were prepared by General Procedure B.

Example 32

N-[4-(3-Methoxyphenyl)butyl]-N'-methyl urea

Synthesized by General Procedure B. The product was isolated as a white solid in 90% yield: mp 74°–75.5° C.; IR (KBr) 3338, 2938, 1622, 1586, 1258, 1152, 1042 cm$^{-1}$; $^1$H NMR (300 MHz, CDCl$_3$) δ 7.15 (t, J=8.1 Hz, 1H), 6.73–6.67 (m, 2H), 6.67 (s, 1H), 4.87 (bs, 2 H), 3.75 (s, 3H), 3.13 (bs, 2H), 2.69 (s, 3H), 2.56 (t, J=7.5 Hz, 2H), 1.65–1.40 (m, 4H); MS m/z 237 (M$^+$+1); Anal. Calcd for $C_{13}H_{20}N_2O_2$: C, 66.07; H, 8.53; N, 11.86. Found: C, 65.88; H, 8.36; N, 11.58.

The following compounds of Formula I were also prepared using General Procedure B.

TABLE 2

| Ex. | Name | mp (° C.) |
| --- | --- | --- |
| 33 | N-Ethyl-N'-[3-(3-methoxyphenyl)-propyl] urea | 57–58 |
| 34 | N-[3-(3-Methoxyphenyl)propyl]-N'-methyl urea | 62–63 |
| 35 | N-[3-(3,4-Dimethoxyphenyl)propyl]-N'-ethyl urea | 69–70 |
| 36 | N-Ethyl-N'-[4-(3-methoxyphenyl)-butyl] urea | 69–70 |
| 37 | N-[3-(2,3-Dimethoxyphenyl)propyl]-N'-ethyl urea | 88–90 |

Compounds of Formula I which were prepared by General Procedure C.

Example 38

N-[3-(3-Methoxyphenyl)propyl]propanamide

Synthesized by General Procedure C. The crude material was purified by silica gel column chromatography using a 5% MeOH/CH$_2$Cl$_2$ eluant to provide a 38% yield of the desired product as an oil. $^1$H NMR (300 MHz, CDCl$_3$) δ 7.14–7.19 (m, 1H), 6.69–6.75 (m, 3H), 5.54 (br s, 1H), 3.76 (s, 3H), 3.22–3.31 (m, 2H), 2.59 (t, J=7.4 Hz, 2H), 2.13 (q, J=7.6 Hz, 2H), 1.80 (quintet, J=7.6 Hz, 2H), 1.10 (t, J=7.6 Hz, 3H); $^{13}$C NMR (75 MHz, CDCl$_3$) δ 173.7, 159.7, 143.1, 129.4, 120.7, 114.1, 111.2, 55.1, 39.1, 33.4, 31.1, 29.7, 9.4; IR (neat) 3300, 1650, 1540 cm$^{-1}$; MS (DCI, isobutane) m/e 443 (MH+M), 222 (MH); Analysis calc'd for C$_{13}$H$_{19}$NO$_2$: C, 70.56; H, 8.65; N, 6.33; found: C, 70.57; H, 8.94; N, 6.16.

Example 39

N-[3-(3-Methoxyphenyl)propyl]acetamide

Synthesized by General Procedure C. The crude material was purified by Kugelrohr distillation to provide an 8% yield of the desired product as an oil. $^1$H NMR (300 MHz, CDCl$_3$) δ 7.14–7.19 (m, 1H), 6.64–6.75 (m, 3H), 5.65 (br s, 1H), 3.76 (s, 3H), 3.20–3.27 (m, 2H), 2.59 (t, J=7.4 Hz, 2H), 1.91 (s, 3H), 1.80 (quintet, J=7.6 Hz, 2H); $^{13}$C NMR (75 MHz, CDCl$_3$) δ 170.1, 159.7, 143.1, 129.4, 120.7, 114.1, 111.2, 55.1, 39.3, 33.3, 31.0, 23.3; IR (neat) 3292, 1652, 1556 cm$^{-1}$; MS (DCI, isobutane) m/e 415 (MH+M), 208 (MH).

Compounds of Formula I which were prepared by General Procedure D.

Example 40

N-[3-(3-Propoxypheny)propyl]butanamide

Synthesized according to General Procedure D. 22% yield of the desired product obtained as a yellow oil. $^1$H NMR (300 MHz, CDCl$_3$) δ 7.19–7.15 (m, 1H), 6.74–6.70 (m, 3H), 5.73 (bs, 1H), 3.88 (t, J=6.6 Hz, 2H), 3.30–3.23 (m, 2H), 260 (t, J=7.3 Hz, 2H), 2.08 (t, J=7.2 Hz, 2H), 1.86–1.75 (m, 4H), 1.61 (sextet, J=7.5 Hz, 2H), 1.02 (t, J=7.3 Hz, 3H), 0.92 (t, J=7.3 Hz, 3H); $^{13}$C NMR (75 MHz, CDCl$_3$) δ 177.9, 159.3, 143.1, 129.4, 120.5, 114.7, 111.8, 69.4, 39.2, 38.7, 33.4, 31.1, 22.6, 19.2, 13.7, 10.5; IR (KBr) 3292, 1644, 1554 cm$^{-1}$; MS (DCI) m/e 527 (MH+M), 264 (MH+); Analysis calc'd for C$_{16}$H$_{25}$NO$_2$: C, 72.97; H, 9.57; N, 5.32; found: C, 72.96; H, 9.22; N, 5.40.

Example 41

N-[3-(3-Ethoxyphenyl)propyl]butanamide.

Synthesized according to General Procedure D. The crude material was purified by silica gel column chromatography using a 40% EtOAc/Hexanes eluant to provide a 61% yield of the desired product as an oil. $^1$H NMR (300 MHz, CDCl$_3$) δ 7.22–7.12 (m, 1H), 6.73–6.68 (m, 3H), 5.57 (bs, 1H), 3.98 (q, J=7.0 Hz, 2H), 3.21–3.28 (m, 2H), 2.58 (t, J=7.3 Hz, 2H), 2.07 (t, J=7.2 Hz, 2H), 1.79 (quintet, J=7.5 Hz, 2H), 1.61 (sextet, J=7.4 Hz, 2H), 1.37 (t, J=7.0 Hz, 3H), 0.90 (t, J=7.4 Hz, 3H); $^{13}$C NMR (75 MHz, CDCl$_3$) δ 172.9, 159.1, 143.1, 129.4, 120.6, 114.7, 111.7, 63.2, 39.1, 38.7, 33.4, 31.1, 19.2, 14.8, 13.7; IR (KBr) 3292, 1644, 1552 cm$^{-1}$; MS (DCI) m/e 499 (MH+M), 250 (MH+).

Example 42

N-[3-(3-Cyclopropylmethoxyphenyl)propyl]-butanamide

Synthesized according to General Procedure D. The crude material was purified by silica gel column chromatography using a 50% EtOAc/hexanes eluant to provide a 76% yield of the desired product as a white solid. m.p. 36°–37° C.; $^1$H NMR (300 MHz, CDCl$_3$) δ 7.24–7.13 (m, 1H), 6.74–6.64 (m, 3H), 5.42 (bs, 1H), 3.76 (d, J=6.9 Hz, 2H), 3.29–3.22 (m, 2H), 2.59 (t, J=7.4 Hz, 2H), 2.08 (t, J=7.2 Hz, 2H), 1.80 (quintet, J=7.5 Hz, 2H), 1.61 (sextet, J=7.4 Hz, 2H), 1.30–1.17 (m, 1H), 0.90 (t, J=7.3 Hz, 3H), 0.65–0.53 (m, 2H), 0.34–0.29 (m, 2H); $^{13}$C NMR (75 MHz, CDCl$_3$) δ 172.9, 159.1, 143.1, 129.4, 120.7, 114.8, 111.9, 72.6, 39.1, 38.7, 33.4, 31.1, 19.2, 13.7, 10.3, 3.1; IR (KBr) 3304, 1636, 1540 cm$^{-1}$; MS (DCI) m/e 551 (2M+H), 276 (MH+); Analysis calc'd for C$_{17}$H$_{25}$N$_1$O$_2$/0.1H$_2$O: C, 73.66; H, 9.16; N, 5.05; H$_2$O, 0.65; found: C, 73.68; H, 9.17; N, 5.04; H$_2$O, 0.25.

Other compounds of formula I were prepared as specified below.

Example 43

3-[3-[(3-Methoxyphenyl)propyl]amino]-3-oxopropanoic acid

The compound was synthesized according to Scheme 7. 3-(3-Methoxyphenyl)propylamine hydrochloride (30 mmol) was free-based in aqueous sodium hydroxide, extracted into CH$_2$Cl$_2$, dried over MgSO$_4$, filtered, and concentrated in vacuo. The resulting oil was dissolved in acetonitrile (100 mL) and powdered potassium carbonate (89 mmol) was added. Ethyl malonyl chloride (30 mmol) was then added to this mixture and the reaction was allowed to stir at RT overnight. The acetonitrile was removed in vacuo and the resulting solid was partitioned between water and CH$_2$Cl$_2$. The organic phase was separated, dried over MgSO$_4$, filtered, and concentrated in vacuo to give the intermediate ester as an oil in 56% yield. A solution of this ester (9.0 mmol) and potassium hydroxide (20 mmol) in a solution of 1:1 methanol/water (150 mL) was heated to reflux for 3 h. The methanol was then removed in vacuo and the aqueous layer was acidified with 1N HCl and extracted with CH$_2$Cl$_2$. The combined organic extracts were dried over MgSO$_4$, filtered, and concentrated in vacuo to provide a white solid which was recrystallized twice from acetonitrile to provide the desired product as a white solid in 12% yield. m.p. 83°–85° C.; $^1$H NMR (300 MHz, CDCl$_3$) δ 7.18 (t, J=9 Hz, 1H), 6.70–6.75 (m, 4H), 3.76 (s, 3H), 3.31 (q, J=7 Hz, 2H), 3.22 (s, 2H), 2.61 (t, J=7 Hz, 2H), 1.83 (quintet, J=7 Hz, 2H); $^{13}$C NMR (75 MHz, CDCl$_3$) δ 169.2, 168.4, 159.7, 142.6, 129.5, 120.6, 114.2, 111.3, 55.1, 39.6, 38.4, 33.2, 30.3; IR (KBr) 2100–3500, 1740, 1640, 1580, 1180 cm$^{-1}$; MS (DCI, isobutane) m/e 252 (MH); Analysis calc'd for $C_{13}H_{17}NO_4$: C, 62.14; H, 6.82; N, 5.57; found: C, 62.48; H, 6.68; N, 5.65.

Measurement of Melatonergic Binding

1. Reagents
   (a) 50mM Tris buffer containing 12.5 mM MgCl2, and 2mM EDTA, pH 7.4 at 37° C. with concentrated HCl.
   (b) Wash buffer: 20mM Tris base containing 2 mM MgCl$_2$. pH 7.4 at room temperature.
   (c) $10^{-1}$M 6-Chloromelatonin ($10^{-5}$M final concentration).
   (d) 2-[$^{125}$I]-iodomelatoin, 44 pM final concentration
   Source: NEN
   Calculations: Concentration of stock: Specific Activity=2200 Ci/mMol Concentration=236 µCi/ml Concentration of stock=(236×10$^{-6}$Ci/ml) / (2200 Ci/mMol)=107.3 nM
   cmp/20 µl (conc.)(liters/tube) = (0.44 × 10$^{-9}$ m/L)(20 × 10$^{-6}$ L) = 8.8 × 10$^{-15}$ m × 1000 ×
by specific activity (8.8 × 10$^{-12}$ mM)(2200 Ci/mMol) = 1.93 × 10$^{-8}$ Ci ×
by decay factor (1.93 × 10$^{-8}$ Ci)(1 on day made) = 1.93 × 10$^{-8}$ Ci ×
by dpm/Ci constant (1.93 × 10$^{-8}$)(2.22 × 10$^{12}$ dpm/Ci) =
42979 dpm × 0.75 (machine efficiency) =
32234 cpm 2. Tissue preparation Male New Zealand white rabbits (Hazelton Research) are decapitated, the brains are rapidly removed and chilled. The parietal cortex is crudely dissected and frozen on dry ice with tissue stored at −80° C. until assayed. Tissue is weighed and thawed in 20 mls ice cold Tris buffer (a) and homogenized by treatment with a polytron for 10 seconds at setting 17. Ice cold Tris (a) is added to a volume of 40 mls. The homogenate is centrifuged in a Sorvall-SS-34 head at 19,000 rpm (44,000×g) for 20 min at 4° C. The resulting supernatant is decanted and discarded. The pellet is rehomogenized in an additional 20 mls of Tris, diluted and centrifuged as before. The supernatant is decanted and discarded. The resulting pellet is homogenized in 20 volumes of Tris per gram of original tissue (a 1:20 homogenate), chilled, and held on ice until assayed.

3. Experimental design

|  | Tube # | Buffer (a) | 10$^{-4}$M 6-Chloromelatonin | Experimental Compound | 2-[125I]-iodo-melatonin | Tissue Homogenate (1:20) |
|---|---|---|---|---|---|---|
| Total | 1,2 | 20 µl | — | — | 20 µl | 160 µl |
| Blank: | 3,4 | — | 20 µl | — | 20 µl | 160 µl |
| Unknowns: | 5,6 | — | — | 20 µl conc. 1 | 20 µl | 160 µl |
|  | 7,8 | — | — | 20 µl conc. 2 | 20 µl | 160 µl |

4. Incubation

37° C. for 1 hour. Reaction is terminated by filtration through a Brandel cell harvester. Filters are washed 3 times.

5. Activity

Compounds with an IC$_{50}$ value less than 500 nM are termed active.

6. References

Stankov, B., Cozzi, B., Lucini, V., Fumagalli, P., Scaglione, F. and F. Fraschini. Characterization and mapping of melatonin receptors in the brain of three mammalian species: Rabbit, horse, and sheep. *Neuroendocrinology* 53: 214–221, 1991.

Table 3 lists some preferred compounds along with their corresponding example numbers:

TABLE 3

Selected Compounds having IC$_{50}$ (nM)* of Less Than 250

| Ex. | Compound Name |
|---|---|
| 1 | 3-[3-(Methoxyphenyl)]propylcyclopropane carboxamide |
| 2 | N-[3-(3-Methoxyphenyl)propyl]butanamide. |
| 6 | cis-N-[3-(2-Fluoro-5-methoxyphenyl)-prop-2-enyl]-butanamide |
| 8 | N-[3-(2,5-Dimethoxyphenyl)propyl]butanamide |
| 17 | N-[4-(3-Methoxyphenyl)butyl]-2-methyl-propanamide |
| 21 | N-[3-(2-Fluoro-5-methoxyphenyl)propyl]-cyclopropane carboxamide |
| 22 | trans-N-[3-(2-Fluoro-5-methoxyphenyl)-2-propenyl]-2-methylpropanamide |
| 26 | N-[3-(3,5-Dimethoxyphenyl)propyl]-butanamide |
| 28 | N-[4-(3-Methoxyphenyl)butyl]cyclobutane carboxamide |

TABLE 3-continued

Selected Compounds having IC$_{50}$ (nM)* of Less Than 250

| Ex. | Compound Name |
|---|---|
| 30 | N-[3-(4-Chloro-3-methoxyphenyl)propyl]-cyclopropane carboxamide |
| 34 | N-[3-(3-Methoxyphenyl)propyl]-N'-methyl urea |
| 36 | N-Ethyl-N'-[4-(3-methoxyphenyl)-butyl] urea |
| 41 | N-[3-(3-Ethoxyphenyl)propyl]butanamide |
| 42 | N-[3-(3-Cyclopropylmethoxyphenyl)propyl]-butanamide |
| 31 | N-[2-(3-Methoxyphenoxy)ethyl]cyclopropane carboxamide |

*IC$_{50}$(nM) is the nanomolar concentration giving displacement of 50% of radioactive label from melatonin binding sites in rabbit parietal cortex tissue.

Measurement of Functional Activity

Cyclic AMP Accumalation in Intact Cells: Melatonin

CELLS

Remove media from cell flask and wash with Hank's salt solution or PBS as appropriate. Detach cells from flask using whatever means are used when splitting. Add enough media so that the concentration of cells is 4×10$^5$/ml when counted with a hemocytometer (40 cells in the center square). This concentration of cells can vary depending on the ultimate cAMP response of the type of cells used. Also, dialyzed fetal bovine serum (FBS) or heat inactivated FBS should be used in the media when plating the cells in case endogenous substances are present in the FBS that might interfere with the test. Add 1 ml of cell suspension to each well ($4\times10^5$ cells/well), then 2 mls of media and incubate cells overnight. SOLUTIONS needed for cyclase:

1. Stock solution: plain media (no serum or additives)+ 20mM HEPES. (500 ml bottle media+10 mls of 1M HEPES GIBCO stock). This solution can be refrigerated and reused.

2. IBMX solution: media/HEPES+1 mM IBMX. (50 mls+11.1 mg IBMX, IBMX mw=222.2). This solution can be refrozen.

3. Assay solution: 90% stock solution+10% IBMX solution. Figure out the volume of solution needed for the assay. Each well gets 3 mls of assay solution for a preincubation and 3 mls for the actual assay, therefore, 6 mls/well. Each test condition is done in triplicate. For example:

```
54 mls stock solution (90%)
+ 6 mls IBMX solution (10%)

= 60 mls assay solution
```

This is enough for 9 wells, 3 conditions. Split solution in half (2×25 ml). Set aside half for preincubation step. The other half will be used to make drug solutions.

4. Drug solutions:

a) Basal 7 mls assay solution + 7 ml DMSO b) Forskolin stimulation: 10 mM final concentration: 7 mls assay solution+7 ml 10 mM forskolin (stock solution in freezer, in DMSO)

c) Forskolin+competitor (melatonin): 10 mM final concentration forskolin: 7 mls assay solution+7 ml 10 mM forskolin+desired concentration of competitor (melatonin). Solutions b) and c) can be combined when adding forskolin, then split before adding competitor.

REACTION

All solutions should be warmed to 37° C. All test conditions are done in triplicate. Plates with cells are kept in a shallow 37° C. water bath throughout the reaction. Remove media from the wells and add 3 ml of preincubation media. After 10 min, remove that solution and add 3 mls of drug solution. After 10 min the media is removed and reaction stopped with 1 ml 0.1 N HCl. Staggering the incubation is recommended. The preincubation step can be eliminated if the cells don't adhere well to the plate or the plates can be pretreated with extracellular matrix such as poly-D-lysine. Let samples set for at least an hour at room temperature. Remove 1 ml from dish and put into a microfuge tube. Do a 3 min spin to remove floating cells. Dilute 1:100 for RIA (this dilution will vary depending on the concentration curve of the RIA kit and the cAMP response and concentration of the cells). Do radioimmunoassay (Amersham: Cat.no. RPA.509).

The functional data for some compounds of Formula I are shown in Table 4.

TABLE 4

| Functional Data of Selected Compounds | | | |
|---|---|---|---|
| Compound Name | Ex. | $EC_{50}$ (nM) | I.A.* |
| N-[3-(3-Methoxyphenyl)propyl] butanamide | 2 | 4.9 | .95 |
| N-[3-(4-Chloro-3-methoxyphenyl) propyl]-cyclopropane carboxamide | 30 | 3.4 | .98 |
| cis-N-[3-(2-Fluoro-5-methoxyphenyl)-2-propenyl]-2-methylpropanamide | 7 | 120 | 1.2 |

*I.A. (Intrinsic Activity) = Emax (experimental compound)/Emax (melatonin)

Reasonable variations, such as those which would occur to a skilled artisan, can be made herein without departing from the scope of the invention.

We claim:

1. A compound of formula I:

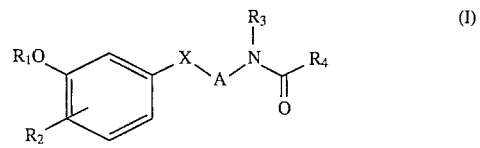

wherein:

$R_1=C_{1}$ alkyl, allyl, $C_{3-6}$ cycloalkyl substituted $C_{1-4}$ alkyl;

$R_2$=hydrogen, halogen or $C_{1-4}$ alkoxy;

$R_3$=hydrogen or $C_{1-4}$ alkyl;

$R_4=C_{1-4}$ alkyl, $C_{3-6}$ cycloalkyl, or straight or branched chain $C_{2-4}$ alkenyl;

A=a linear $C_{2-4}$ alkanediyl or alkenediyl chain, provided that A not be —$CH_2CH_2$— when X is a bond; and X=a covalent bond or oxygen.

2. The compound of claim 1 wherein $R_3$ is hydrogen and X is a convalent bond.

3. The compound of claim 2 wherein $R_1$ is methyl, A is $C_3$ alkenediyl and $R_4$ is $C_{1-4}$ alkyl.

4. The compound of claim 3 wherein $R_2$ is fluoro.

5. The compound of claim 4 selected from the group consisting of:

trans-N-[3-(2-fluoro-5-methoxyphenyl)-2-propenyl]-2-methylpropanamide;

cis-N-[3-(2-fluoro-5-methoxyphenyl)-2-propenyl]-2-methylpropanamide; and cis-N-[3-( 2-fluoro-5-methoxyphenyl)-2-propenyl]butanamide.

6. The compound of claim 2 wherein A is $C_{3-4}$ alkanediyl and $R_4$ is $C_{1-4}$ alkyl or $C_{3-6}$ cycloalkyl.

7. The compound of claim 6 selected from the group consisting of:

N-[3-(4-chloro-3-methoxyphenyl)propyl]cyclopropane carboxamide;

N-[3-(3-cyclopropylmethoxyphenyl)propyl]butanamide;

N-[3-(3-propoxyphenyl)propyl]butanamide; and

N-[3-(3-ethoxyphenyl)propyl]butanamide.

8. The compound of claim 6 wherein $R_1$ is methyl.

9. The compound of claim 8 selected from the group consisting of:

N-[3-(3,4-dimethoxyphenyl)propyl]butanamide;

N-[3-(3,4-dimethoxyphenyl)propyl]cyclopropane carboxamide;

N-[3-(3,5-dimethoxyphenyl)propyl]butanamide;

N-[3-(2,5-dimethoxyphenyl)propyl]butanamide;
N-[3-(3-methoxyphenyl)propyl]cyclopropane carboxamide;
N-[3-(3-methoxyphenyl)propyl]butanamide;
N-[3-(3-methoxyphenyl)propyl]-2-methylpropanamide;
N-[3-(2,5-dimethoxyphenyl)propyl]cyclopropane carboxamide;
N-[3-(3-methoxyphenyl)propyl]propanamide;
N-[3-(2,3-dimethoxyphenyl)propyl]butanamide;
N-[3-(2-fluoro-5-methoxyphenyl)propyl]cyclopropane carboxamide;
N-[3-(2-fluoro-5-methoxyphenyl)propyl]butanamide;
N-[3-(2-fluoro-5-methoxyphenyl)propyl]-2-methylpropanamide;
N-[3-(2-fluoro-5-methoxyphenyl)propyl]acetamide;
N-[3-(3-methoxyphenyl)propyl]pentanamide;
N-[4-(3-methoxyphenyl)butyl]cyclopentane carboxamide;
N-[4-(3-methoxyphenyl)butyl]cyclobutane carboxamide;
N-[4-(3-methoxyphenyl)butyl]pentanamide;
N-[4-(3-methoxyphenyl)butyl]butanamide;
N-[4-(3-methoxyphenyl)butyl]propanamide;
N-[4-(3-methoxyphenyl)butyl]cyclopropane carboxamide;
N-[3-(3-methoxyphenyl)propyl]acetamide;
N-[4-(3-methoxyphenyl)butyl]acetamide; and
N-[4-(3-methoxyphenyl)butyl]-2methylpropanamide.

10. The compound of claim 1 selected from the group consisting of:
N-[2-(3-methoxyphenoxy)ethyl]cyclopropane carboxamide;
N-[2-(3-methoxyphenoxy)ethyl]butanamide;
N-[3-(3-methoxyphenyl)propyl]propenamide;
N-[3-(3-methoxyphenyl)propyl]-2-methyl propenamide.

11. The compound of claim 1 wherein $R_1$ is methyl, $R_2$ is hydrogen, $R_4$ is $C_{1-3}$ linear alkyl or cyclopropyl, A is $C_{3-4}$ alkanediyl and X is a covalent bond.

12. N-[3-(3-methoxyphenyl)propyl]cyclopropane carboxamide.

13. N-[3-(3-methoxyphenyl)propyl]butanamide.

14. A pharmaceutical composition for treating a sleep or circadian rhythm disorder in a patient in need thereof comprising an effective amount of the compound of claim 1 and a suitable amount of a pharmaceutically acceptable carrier.

15. The composition of claim 14 containing from about 0.1 to about 10 weight % of a compound of claim 1.

16. A method of treating a sleep or circadian rhythm disorder in a patient in need of such treatment comprising the administration of an effective amount of a compound of claim 1.

17. The method of claim 16 wherein the amount used is from about 0.1 mg to about 100 mg per dose.

* * * * *

UNITED STATES PATENT AND TRADEMARK OFFICE
CERTIFICATE OF CORRECTION

PATENT NO: 5,541,228
DATED : July 30, 1996
INVENTOR(S): Takaki et al.

It is certified that error appears in the above-identified patent and that said Letters Patent is hereby corrected as shown below:

In claim 1, column 26, line 29, change "$R_1=C_1-$" to --$R_1=C_{1-3}$--.

Signed and Sealed this

Thirty-first Day of December, 1996

Attest:

BRUCE LEHMAN

Attesting Officer

Commissioner of Patents and Trademarks